(12) United States Patent
Yan et al.

(10) Patent No.: US 9,119,803 B2
(45) Date of Patent: Sep. 1, 2015

(54) CARIOUS TOOTH VACCINE AND PREPARATION METHOD

(75) Inventors: Huimin Yan, Wuhan (CN); Wei Shi, Wuhan (CN); Ying Sun, Wuhan (CN); Jingyi Yang, Wuhan (CN)

(73) Assignee: Wuhan Institute of Virology, Chinese Academy of Sciences, Wuhan (CN)

( * ) Notice: Subject to any disclaimer, the term of this patent is extended or adjusted under 35 U.S.C. 154(b) by 0 days.

(21) Appl. No.: 14/234,145

(22) PCT Filed: Dec. 29, 2011

(86) PCT No.: PCT/CN2011/084876
§ 371 (c)(1),
(2), (4) Date: Jan. 21, 2014

(87) PCT Pub. No.: WO2013/091260
PCT Pub. Date: Jun. 27, 2013

(65) Prior Publication Data
US 2014/0161836 A1    Jun. 12, 2014

(30) Foreign Application Priority Data
Dec. 23, 2011    (CN) .......................... 2011 1 0438088

(51) Int. Cl.
*A61K 39/09* (2006.01)
*A61K 39/02* (2006.01)
*A61K 39/00* (2006.01)

(52) U.S. Cl.
CPC .............. *A61K 39/092* (2013.01); *A61K 39/09* (2013.01); *A61K 2039/543* (2013.01); *A61K 2039/55594* (2013.01)

(58) Field of Classification Search
CPC ....... A61K 38/00; A61K 38/16; A61K 39/00; A61K 39/02; A61K 39/09
USPC ........ 424/9.1, 9.2, 184.1, 185.1, 234.1, 244.1
See application file for complete search history.

(56) References Cited

FOREIGN PATENT DOCUMENTS

CN         101411872      *   4/2009

OTHER PUBLICATIONS

Lehner et al., Immunization with Purified Protein Antigens from *Streptococcus* mutans Against Dental Caries in Rhesus Monkeys. Infection and Immunity 34, 407-415 (1981).
Saito et al. Protective Immunity to *Streptococcus* mutans Induced by Nasal Vaccination with Surface Protein Antigen and Mutant Cholera Toxin Adjuvant.

* cited by examiner

*Primary Examiner* — Rodney P Swartz
(74) *Attorney, Agent, or Firm* — George Dacai Liu

(57) ABSTRACT

The present invention provides a vaccine composition for dental caries caused by *S. mutans* infection, where the vaccine composition comprises an antigen derived from a surface protein PAc of *S. mutans* and an adjuvant derived from flagellin. The present invention further provides methods for preparing the vaccine composition. The present invention also provides methods for preventing or curing dental caries caused by *S. mutans* by administrating to a subject the vaccine composition.

9 Claims, 15 Drawing Sheets

(a)

(b)

(A)

(B)

(A)

(B)

CARIOUS TOOTH VACCINE AND PREPARATION METHOD

FIELD OF THE INVENTION

The present invention generally relates to the technologies of vaccines, and more particularly to a dental caries vaccine and further to methods for preparing the vaccine.

BACKGROUND OF THE INVENTION

*Streptococcus mutans* (*S. mutans*) has been implicated as the primary etiological bacteria causing dental caries in human. *S. mutans* expresses a surface protein, designated as antigen I/II, B, P1, or PAc. PAc is involved in the initial adherence of *S. mutans* to tooth surface and the later aggregation of *S. mutans* on the tooth surface; thus PAc is considered a crucial virulence factor, contributing to the pathogenesis of dental caries. Due to its importance in the cariogenicity of *S. mutans*, PAc is recognized as a target for development of anti-caries vaccines.

*Streptococcus mutans* (*S. mutans*) has been implicated as the primary etiological bacteria causing dental caries in human. *S. mutans* expresses a surface protein, designated as antigen I/II, B, P1, or PAc. PAc is involved in the initial adherence of *S. mutans* to tooth surface and the later aggregation of *S. mutans* on the tooth surface; thus PAc is considered a crucial virulence factor, contributing to the pathogenesis of dental caries. Due to its importance in the cariogenicity of *S. mutans*, PAc is recognized as a target for development of anti-caries vaccines.

In one early study, Lehner et al. (Immunization with Purified Protein Antigens from *Streptococcus mutans* Against Dental Caries in Rhesus Monkeys. *Infection and Immunity* 34, 407-415 (1981)) had purified protein antigens I, I/II, II, and III from bacterial culture directly. The purified antigens were intramuscularly administered with adjuvant (Freund incomplete adjuvant or aluminum hydroxide). Antigens I, I/II and, to a lesser extent, antigen II induced significant reductions in dental caries, but thre was no reduction in caries with antigen III. Protection against caries was associated predominantly with serum and gingival crevicular fluid IgG antibodies. Under the immunization schemes used in this study, serum IgA antibodies showed titers of between $\log_2$ 0.7 and 2.8. However, the purities of the antigens used in the experiments were in question. In addition, the claimed effectiveness might be attributed to the administration route—intramuscular.

Due to the infection mode of *S. mutans*, mucosal immunity shall be preferable for developing an effective vaccine. Unfortunately, numerous studies have shown that PAc without an appropriate adjuvant is a weak immunogen when given via the mucosal routes. In order to address this, Saito et al. (Protective Immunity to *Streptococcus mutans* Induced by Nasal Vaccination with Surface Protein Antigen and Mutant Cholera Toxin Adjuvant. *Journal of Infectious Diseases* 183, 823-826 (2001)) purified PAc from the cultural supernatant of *S. mutans*. Nasal administration of FAc and mutant cholera toxin (mCT) induced PAc-specific IgA antibodies with the titers in saliva (log 2, 6.1+/−1.7) and in nasal wash samples (log 2, 8.2+/−1.5). Ag-specific immune responses induced by nasal immunization with PAc with mCT provided significant inhibition of colonization of *S. mutans*. However, this study has critical shortcomings. First, the antigen PAc used was not an expressed recombinant protein; direct purification from bacterial cultures could not rule out the possibility that the shown effectiveness resulted from the contamination; this is similar to Lehner study described above. Second, cholera toxin (CT) is toxic; although it has been studied for many years, it is still far away from human uses. Finally, the effectiveness of protection against dental caries was not directly shown.

In summary, while the prior arts have indicated that PAc might be a possible antigen for developing vaccines against the dental caries caused by *S. mutans*, there is no teaching or suggestion of what an effective mucosal vaccine against the dental caries caused by *S. mutans* should be.

Therefore, there is an imperative need to develop an effective mucosal vaccine against the dental caries caused by *S. mutans*.

SUMMARY OF THE INVENTION

The present invention provides a vaccine composition for dental caries caused by *S. mutans* infection, where the vaccine composition comprises an antigen derived from a surface protein PAc of *S. mutans* and an adjuvant derived from flagellin. The present invention further provides methods for preparing the vaccine composition. The present invention also provides methods for preventing or curing dental caries caused by *S. mutans* by administrating to a subject the vaccine composition.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

DETAILED DESCRIPTION OF THE INVENTION

Figure 1:
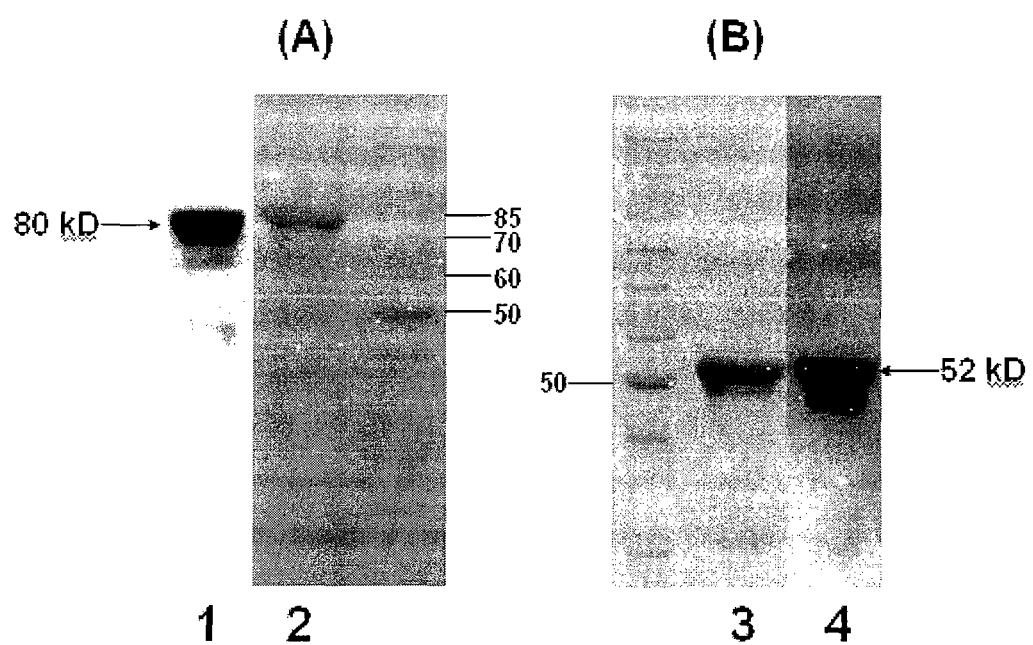
FIG. 1 shows the purified PAc and FliC (flagellin); (A) lane 1: Western blot of purified PAc probed with HRP-conjugated anti-His-tag antibody; lane 2: Coomassie blue stain of SDS-PAGE of the purified recombinant PAc; (B) Lane 3: Coomassie blue stain of SDS-PAGE of the recombinant FliC; and lane 4: Western blot of purified FliC probed with HRP-conjugated anti-His-tag antibody.

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, for example, *Molecular Cloning: A Laboratory Mannual*, second edition (Sambrook et al., 1989); *Current Protocols in Molecular Biology* (F. M. Ausubel et al., eds., 1987).

One aspect of the present invention provides a vaccine used as a preventive or therapeutic medicament against the dental caries caused by *S. mutans* infection. In one embodiment, the vaccine of the present invention comprises a surface antigen (PAc) from *S. mutans* and flagellin as adjuvant. In certain embodiments, the PAc and flagellin are expressed separately and mixed when they are employed to manufacture the vaccine; in certain embodiments, the PAc and flagellin are expressed as a single recombinant protein, for example the PAc is inserted into the hypervariable domain of the flagellin or substitutes partial or whole hypervariable domain of the flagellin; in certain embodiments, the PAc and flagellin are tagged or conjugated with complementary moieties that bring these two molecules into close proximity; in certain embodiments, the PAc and flagellin are conjugated; in certain embodiments, the PAc and flagellin are bound to a carrier that brings these two molecules into close proximity.

In certain embodiments, the PAc antigen is the full length protein (SEQ ID NO 2). In certain embodiments, the PAc antigen is an edited version of the full length protein where the edited version comprises the main antigenic epitopes. The edited version means that one or more main antigenic epitopes of PAc are expressed in a recombinant protein, where the epitopes are either directly coupled or separated by a number of amino acids so long to maintain their antigenic conformation.

A "variant" used throughout this application refers to a polypeptide that is functional and has at least 90% identity with the sequences identified in the Sequence Listing, more preferably has at least 95% identity. For example, for PAc, a variant of PAc refers to a polypeptide that is antigenic useful for inducing immune response to PAc and has at least 90% identity with sequence listed in SEQ ID NO 1.

In certain embodiments, the fusion protein comprises a cleavable linker that is disposed between the PAc and purification tag, affording the removal of the tag from the fusion protein by chemical or enzymatic treatment of the fusion protein. It is apparent that the cleavable linker can be disposed at any site of the fusion protein according to a user's desire. In the expression vectors, the cleavable linker comprises a DNA sequence which codes for an amino acid or a sequence of amino acids which can be cleaved chemically or enzymatically at its C-terminal.

Examples of chemical agents useful for cleaving proteins are cyanogen bromide, 2-(2-nitrophenyisulfenyl)-3-bromo-3'-methylindolinium (BNPS-skatole), hydroxylamine, and the like. Cyanogen bromide cleaves proteins at the C-terminal of a methionine residue. BNPS-skatole cleaves at the C-terminal of a tryptophan residue. Hydroxylamine cleaves at the C-terminal of the moiety -Asn-Z- in which Z is Gly, Leu, or Ala.

Examples of enzymatic agents useful for cleavage are trypsin, papain, pepsin, plasmin, thrombin, enterokinase, and the like. Each effects cleavage at a particular amino acid sequence which it recognizes. Enterokinase, for example, recognizes the amino acid sequence -(Asp)$_n$-Lys- in which n is an integer from 2 to 4.

In certain embodiments, the fusion protein comprises one or more other purification tags. For example, six histidine residues are fused to the PAc at its N- or C-terminals, allowing purification of the PAc by a $Ni^{2+}$ column. After the purification, six histidine residues can be removed by chemical or enzymatic cleavage. In fact, any known purification tag is suitable here including myc tag, Flag-peptide, KT3 epitope, alpha-tubulin epitope, T7 gene 10 protein peptide tag, glutathione-S-transferase (GST), strep-tag, bovine pancreatic trypsin inhibitor (BPTI), and maltose binding protein (MBP).

As discussed above, the techniques for expression vector cloning, construction and amplification are well known to those skilled in the art. Therefore, the expression vectors for PAc or FliC can be constructed by routine procedures; no further details are provided herein in order not to obscure the present invention.

The mucosal surface is the most important protective barrier to the body, which is due to the predominant isotype, S-IgA, a product of the common mucosal immune system (CMIS). There are several mucosal routes which are developed for local immunization including oral, gastric instillation, intranasal, pulmonary, vaginal and rectal routes. Compared with other mucosal routes, intranasal immunization has more advantages, like being more convenient to administer and being easier to eliciting mucosal response especially in oral cavity. Intranasal administration is a convenient delivery route and has been demonstrated to be effective in inducing salivary IgA responses in anti-caries vaccination.

As used herein, a "vaccine" is an antigenic preparation that is used to induce an immune response in individuals. A vaccine can have more than one constituent that is antigenic.

As used herein, "non-protein carriers" are carriers which are not proteins and can be used to achieve multimeric display of PAc and flagellin antigenic epitopes.

The term "microcarrier" refers to a particulate composition which is insoluble in water and which has a size of less than about 150, 120 or 100 µm, more commonly less than about 50-60 µm, and may be less than about 10 µm or even less than about 5 µm. Microcarriers include "nanocarriers," which are microcarriers have a size of less than about 1 µm, preferably less than about 500 nm. Microcarriers include solid phase particles such particles formed from biocompatible naturally occurring polymers, synthetic polymers or synthetic copolymers, although microcarriers formed from agarose or cross-linked agarose may be included in the definition of microcarriers herein as well as other bio degradable materials known in the art. Solid phase microcarriers are formed from polymers or other materials which are non-erodible and/or non-degradable under mammlian physiological conditions, such as polystyrene, polypropylene, silica, ceramic, polyacrylamide, gold, latex, hydroxyapatite, and ferromagnetic and paramagnetic materials. Biodegradable solid phase microcarriers may be formed from polymers which are degradable (e.g., poly(lactic acid), poly(glycolic acid) and copolymers thereof, such as poly(D, L-lactide-co-glycolide) or erodible (e.g., poly(ortho esters such as 3,9-diethylidene-2,4,8,10-tetraoxaspiro [5,5] undecane (DETOSU) or poly(anhydrides), such as poly(anhydrides) of sebacic acid) under mammalian physiologicaly conditions. Microcarriers are typically spherical in shape, but microcarriers which deviate from spherical shape are also acceptable (e.g., ellipsoidal, rod-shaped, etc.). Microcarriers may also be liquid phase (e.g., oil or lipid based), such as liposomes, iscoms (immune-stimulating complexes, which are stable complexes of cholesterol, phospholipid and adjuvant-active saponin) without antigen, or droplets or micelles found in oil-in-water or water-in-oil emulsions, such as MF59. Biodegradable liquid phase microcarriers typically incorporate a biodegradable oil, a number of which are known in the art, including squalene and vegetable oils. The term "nonbiodegradable", as used herein, refers to a microcarrier which is not degraded or eroded under normal mammalian physiological conditions. Generally, a microcarrier is considered nonbiodegradable if it no degraded (i.e., loses less than 5% of its mass or average polymer length) after a 72 hour incubation at 37° C. in normal human serum.

An "individual" or "subject" is a vertebrate, such as avian, preferably a mammal, such as a human. Mammals include, but are not limited to, humans, non-human primates, farm animals, sport animals, experimental animals, rodents (e.g., mice and rats) and pets.

An "effective amount" or a "sufficient amount" of a substance is that amount sufficient to effect a desired biological effect, such as beneficial results, including clinical results, and as such, an "effective amount" depends upon the context in which it is being applied. In the context of this invention, an example of an effective amount of a composition comprising the desired antigen is an amount sufficient to induce an immune response in an individual. An effective amount can be administered in one or more administrations.

"Stimulation" of an immune response, such as humoral or cellular immune response, means an increase in the response, which can arise from eliciting and/or enhancement of a response.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of infection, stabilized (i.e., not worsening) state of infection, amelioration or palliation of the infectious state, and remission (whether partial or total), whether detectable or undetectable. "Treatment" can also mean prolonging survival as compared to expected survival if not receiving treatment.

According to the present invention, a "dose" of a vaccine composition, is a quantity of vaccine composition that is administered at a particular point in time. A "dose" may also be a quantity of vaccine composition that is gradually administered to an individual using an extended release formulation and/or apparatus. In certain embodiments of the present invention, two or more doses of the vaccine composition are administered to an individual at different time points.

According to the present invention, an "immunologically-effective amount" of PAc is an amount of PAc which will induce complete or partial immunity in a treated animal against subsequent challenge with *S. mutans*. Complete or partial immunity can be assessed by observing, either qualitatively or quantitatively, the clinical symptoms of dental caries in a vaccinated individual as compared to an unvaccinated individual after being challenged. Where the clinical symptoms in a vaccinated individual after challenge are reduced, lessened or eliminated as compared to the symptoms observed in an unvaccinated individual after a similar or identical challenge, the amount of PAc that was administered to the vaccinated individual is regarded as an "immunologically-effective amount".

Unless defined otherwise, all technical and scientific terms used herein have the same meaning as commonly understood by one of ordinary skill in the art to which this invention belongs.

The dose of PAc is between 0.1 and 60 µg. Preferably, the dose of PAc is between 0.25 and 15 µg. Most preferably, the dose is between 1 and 3 µg.

The vaccine of the present invention may further comprise another adjuvant. Non-limiting examples of suitable adjuvants include squalane and squalene (or other oils of animal origin); block copolymers; detergents such as Tween-80; Quil A, mineral oils such as Drakeol or Marcol, vegetable oils such peanut oil; *Corynebacterium*-derived adjuvants such as *Corynebacterium parvum*; *Mycobacterium bovis* (Bacille Calmette and Guerin or BCG); interleukins such as interleukin 2 and interleukin 12; monokines such as interleukin 1; tumor necrosis factor; interferons such as gamma interferon; surface active substances such as hexadecylamine, octadecylamine, octadecyl amino acid esters, lysolecithin; oil emulsions; and mineral gels such as aluminum phosphate, aluminum hydroxide or alum.

A therapeutic composition of the present invention can be formulated in an excipient that the object to be treated can tolerate. Examples of such excipienis include water, saline, Ringer's solution, dextrose solution, Hank's solution, and other aqueous physiologically balanced salt solutions. Excipients can also contain minor amounts of additives, such as substances that enhance isotonicity and chemical or biological stability. Examples of buffers include phosphate buffer, bicarbonate buffer, and Tris buffer, while examples of stabilizers include A1/A2 stabilizer.

Acceptable protocols to administer therapeutic compositions in an effective manner include individual dose size, number of doses, frequency of dose administration, and mode of administration. Determination of such protocols can be accomplished by those skilled in the art, and examples are disclosed herein.

Administering or administer is defined as the introduction of a substance into the body of an individual and includes oral, nasal, ocular, rectal, vaginal and parenteral routes. Compositions may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN) or orally.

The dose administered to a patient, in the context of the present invention, should be sufficient to effect a beneficial response in a patient over an appropriate period of time. The quantity of agents to be administered may depend on the subject to be treated inclusive of the age, sex, weight and general health condition thereof.

Immunotherapeutic compositions of the invention may be used to prophylactically or therapeutically immunize individuals such as humans. However, other animals are contemplated, preferably vertebrate animals including domestic animals such as livestock and companion animals.

Pharmaceutically acceptable carriers preferred for use in the present invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose", and the like. Preservatives and other additives may also be present such as, for example, antimicrobials, antioxidants, chelating agents, and inert gases and the like.

The following examples are provided for the sole purpose of illustrating the principles or implementation of the present invention; they are by no means intended to limit or narrow the scope of the present invention.

EXAMPLE 1

Bacteria

*S. mutans* Ingbritt was grown in brain heart infusion (BHI) broth for 18 h at 37° C. under anaerobic condition, and the cultures were used for infection or stored in glycerol-BHI broth at −70° C. until used.

Expression and Purification of recombinant PAc and FliC
pVAX1 is the only vector authorized by the US Food and Drug Administration in clinical trials.

The genes and proteins of PAc and flagellin used are represented by SEQ ID NO 1 (coding sequence of PAc), SEQ ID NO 2 (PAc protein), SEQ ID NO 3 (coding sequence of flagellin), and SEQ ID NO 4 (flagellin protein). The fragment of PAc (aa 219-680) encoded by nucleotides (657-2694) and the FliC were amplified from pertinent bacterial strains and cloned into expression plasmid pET28a using conventional recombinant techniques, resulting in pET28a-PAc or pET28a-FliC respectively. The recombinant PAc and FliC proteins at their C-terminal were fused with a 6HisTag for facilitating purification. Expression plasmids pET28a-PAc or pET28a-FliC were respectively transformed into *E. coli* BL21 (DE3), and single positive clones were verified. The transformed bacteria were cultured overnight at 37° C. in Luria-Bertani (LB) broth with 50 µg/ml Kanamycin; bacteria of logarithmic phase were induced with 0.5 mM isopropyl β-D-thiogalactoside (IPTG). The expressed recombinant proteins were purified by affinity chromatography on a Ni-NTA column (Qiagen); the purified proteins were quantified by Bradford method and verified by Western blot with a murine anti-HigTag mAb (Qiagen) and a second horseradish-peroxidase-conjugated goat anti-mouse antibody (Pierce). The detection for Western blot was performed with the SuperSignal West Pico Chemiluminescent Substrate (Piece), followed by imaging on a Versadoc 3000 Imager (Bio-Rad). Contaminated endotoxins and lipopolysaccharides (LPS) were removed using AffinityPak Detoxi Gel Endotoxin Removing Gel (Piece). The contents of endotoxin and LPS in the final protein preparations were determined using Limulus assay (Associates of Cape Cod); the values were <0.001 EU/µg.

EXAMPLE 2

Immunization of Mice

For dose effect, four groups of 8-weeks-old female BALB/c mice (n=5) were intranasally (i.n.) immunized three times at 24-day intervals with (1) PBS, (2) 10 µg PAc, (3) 10 µg PAc+1 µg FliC, or (4) 10 µg PAc+5 µg FliC for each mouse with a volume of 10 µl, where all proteins were dissolved in PBS. Sera and saliva were collected 4 weeks after final immunization. Anesthetized animals were bled, and then sera were obtained from centrifugation of blood samples. Saliva samples were collected after intraperitoneal (i.p.) injection of (50 µl for mice; 250 µl for rats) 200 µg/ml carbachol (Sigma) to stimulate flow. The saliva samples needed to be centrifuged before antibody analysis. Sera and saliva were stored at −70° C. until they were assayed by ELISA.

For long-lasting effect, three groups of 8-week-old female BALB/c mice (n=5) were intranasally (i.n.) immunized three times at 24-day intervals with (1) PBS, (2) 10 µg PAc, or (3) 10 µg PAc+5 µg FliC for each mouse with a volume of 10 µl, where all proteins were dissolved in PBS. Sera and saliva were collected at indicated times after final immunization as described above.

For dose effects in rats, four groups of female Wistar rats (n=5) were intranasally (i.n.) immunized three times at 24-day intervals with: (1) PBS; (2) 5 µg FliC; (3) 20 µg PAc+5 µg FliC; (4) 40 µg PAc+5 µg FliC for each rat with a volume of 10 µl, where all proteins were dissolved in PBS. Salivary and blood samples were collected at week 3, 6, 9, 10.

EXAMPLE 3

Experimental Rat Model

Six groups of female Wistar rats (n=5) were weaned at 18 days of age and fed with cariogenic diet, Keyes 2000. Antibiotics (ampicillin, chloramphenicol, and carbenicillin, 1.0 g/kg diet or water) were added from days 20 to 22 to temporarily suppress the oral flora to facilitate cariogenic bacterial colonization. From days 24 to 26, the rats were orally challenged with 1×10⁹ CFU of S. mutans Ingbritt by the use of swabs presoaked with the bacterial solution. Bacterial samples of the tooth surfaces were examined to verify that each rat was infected.

The scheme for therapeutic studies was as follows. Days 0-3 were for adaptive feeding; days 4-8 for elimination of oral bacteria by feeding with antibiotics; days 9-14 for planting S. mutans onto teeth; day 14 for prime vaccination; days 39 and 64 for boosting. The scheme for preventive studies was as follows. Days 0-3 were for adaptive feeding; Day 3 for prime vaccination; Days 28 and 52 for boosting; Days 35-40 for elimination of oral bacteria by feeding with antibiotics; days 41-46 for planting S. mutans onto teeth. Four groups of rats were intranasally immunized with: (1) PBS; (2) 5 μg FliC; (3) 20 μg PAc+5 μg FliC; (4) 40 μg PAc+5 μg FliC, respectively, following the schemes as described above.

EXAMPLE 4

Antibody Analysis

For murine samples, specific saliva secretory IgA (S-IgA) and serum IgG and IgA were detected by ELISA. Polystyrene 96-well ELISA flat-bottom microplates (Greiner bio-one, Germany) were coated at 37° C. for 3 h with 100 μl PAc (5 μg/ml in carbonate buffer, pH 9.6). After blocked with PBS containing 1% bovine serum albumin (BSA) overnight at 4° C., the plates were washed three time, and serially diluted saliva or sera were added to each well and incubated at 37° C. for 2 h. The plates were washed six times with PBS containing 0.05% Tween 20 (PBST) before the addition of 100 μl alkaline phosphatase-conjugated goat anti-mouse IgG and goat anti-mouse IgA (diluted 1:2000, SouthernBiotech). After washed six times with PBST, 100 μl phosphate substrate (p-nitrophenylphosphate) was then added to each well. After incubated at 37° C. for 30 min, optical density at 405 nm (OD 405) was recorded. The end-point titer was defined as the highest dilution with an absorbance=0.1 over the absorbance of the sham control (no sample added).

For rat samples, Polystyrene 96-well ELISA flat-bottom microplates (Greiner bio-one, Germany) were coated at 37° C. for 3 h with 100 μl PAc (5 μg/ml in carbonate buffer, pH 9.6). After blocked with PBS containing 1% bovine serum albumin (BSA) overnight at 4° C., the plates were washed three times, and serially diluted saliva or sera were added to each well and incubated at 37° C. for 2 h. Each well was washed again with PBST, and then treated with 100 μl quantities of goat anti-rat IgG or IgA (1:1000; Sigma), incubated for 2 h at 37° C., and washed again. Next, a 100 μl quantity of alkaline-phosphatase-conjugated rabbit anti-rat IgG (1:10, 000; SouthernBiotech) was added to each well and incubated for 5 h at 37° C., followed by phosphate substrate (p-nitrophenylphosphate) for 30 min at 37° C. Optical density (OD) readings were taken at 405 nm. The end-point titer was defined as the highest dilution with an absorbance=0.1 above that of the sham control (no sample added).

EXAMPLE 5

Rat Caries Assessment

After collecting the sera and saliva samples, rats were sacrificed and mandibles were removed, cleaned, and stained with murexide. Then the molar teeth were washed and sectioned and the caries levels were determined by the Keyes method. The extension and depth of carious lesions were scored as enamel (E), superficial dentinal (Ds), and moderate dentinal (Dm) involvement. The overall carious score was the sum of E, Ds and Dm scores.

EXAMPLE 6

Statistical Analysis

Statistical differences were analyzed by using the Student t test. All animal experiments were repeated at least three times, and results from a representative experiment are shown.

EXAMPLE 7

Results

The recombinant PAc and FliC were purified and verified by anti-PAc and anti-His-tag antibody as an 85 kD band (FIG. 1, lane 1) and a 52 kD band (FIG. 1, lane 4).

Figure 2:
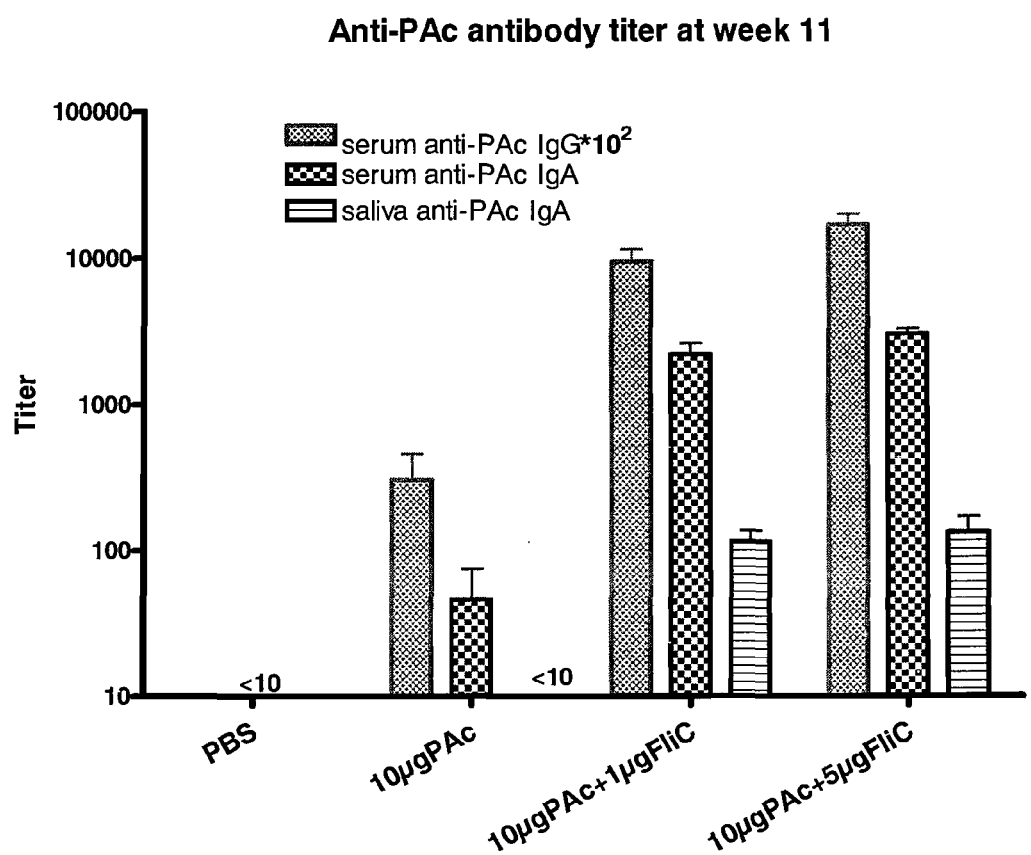
FIG. 2 is a graph showing the titers of serum anti-PAc IgG, serum anti-PAc IgA and saliva anti-PAc IgA antibodies from four groups of mice intranasally immunized with: (1) PBS; (2) 10 μg PAc; (3) 10 μg PAc+1 μg FliC; (4) 10 μg PAc+5 μg FliC, where the data are expressed as means±standard deviation.

Referring to FIG. 2, there is provided a graph showing the antibody titers from the mice that were intranasally immunized with with (1) PBS, (2) 10 μg PAc, (3) 10 μg PAc+1 μg FliC, or (4) 10 μg PAc+5 μg FliC. The results showed that FliC was a potent enhancer for augmenting the anti-PAc antibody titers in the sera and saliva, and more importantly, in the presence of FliC, PAc was capable of inducing high level of specific anti-PAc IgG and IgA antibodies in both sera and saliva.

Figure 3:
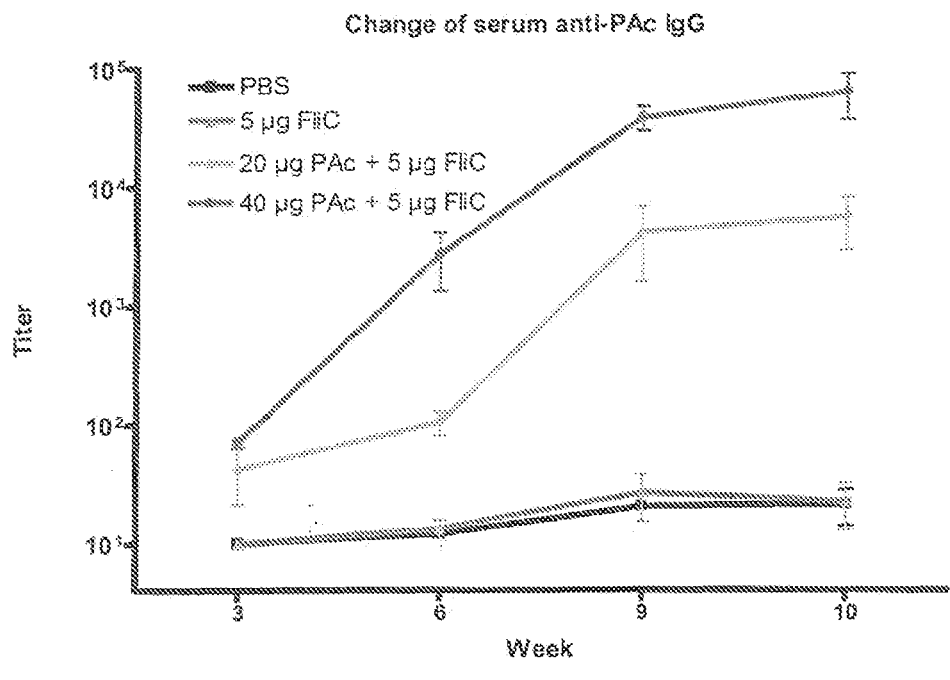
FIG. 3 is a graph showing the titers of (a) serum anti-PAc IgG, (b) serum anti-PAc IgA and (c) saliva anti-PAc IgA antibodies from four groups of rats intranasally immunized with: (1) PBS; (2) 5 μg FliC; (3) 20 μg PAc+5 μg FliC; (4) 40 μg PAc+5 μg FliC, where the data are expressed as means±standard deviation.
Figure 3:
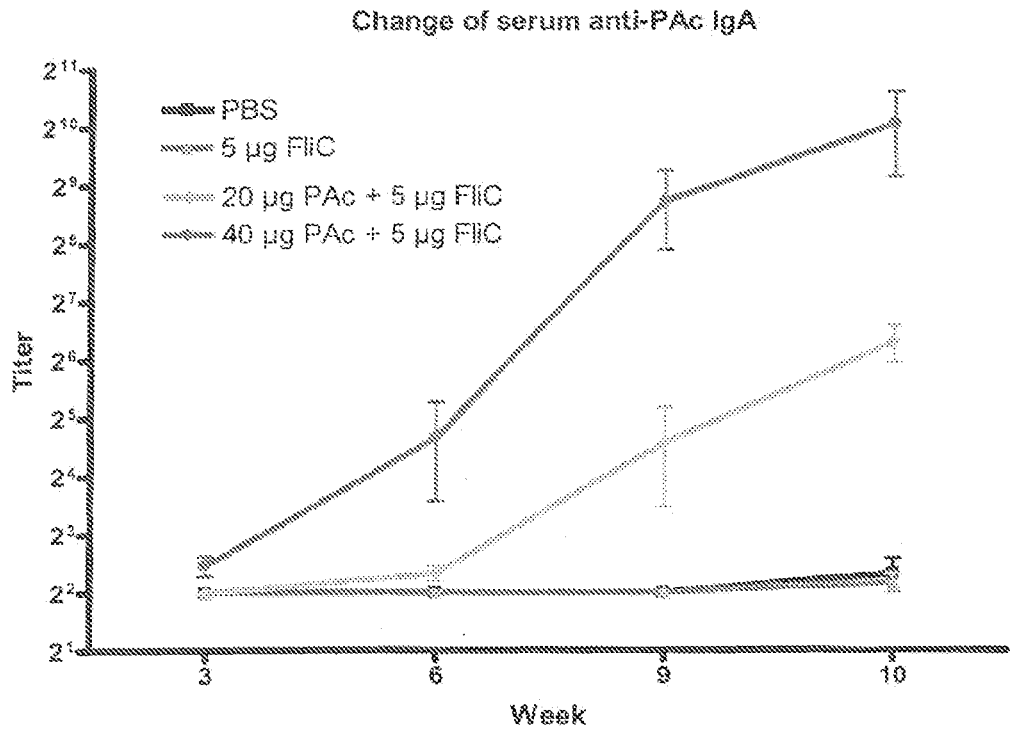
Figure 3:
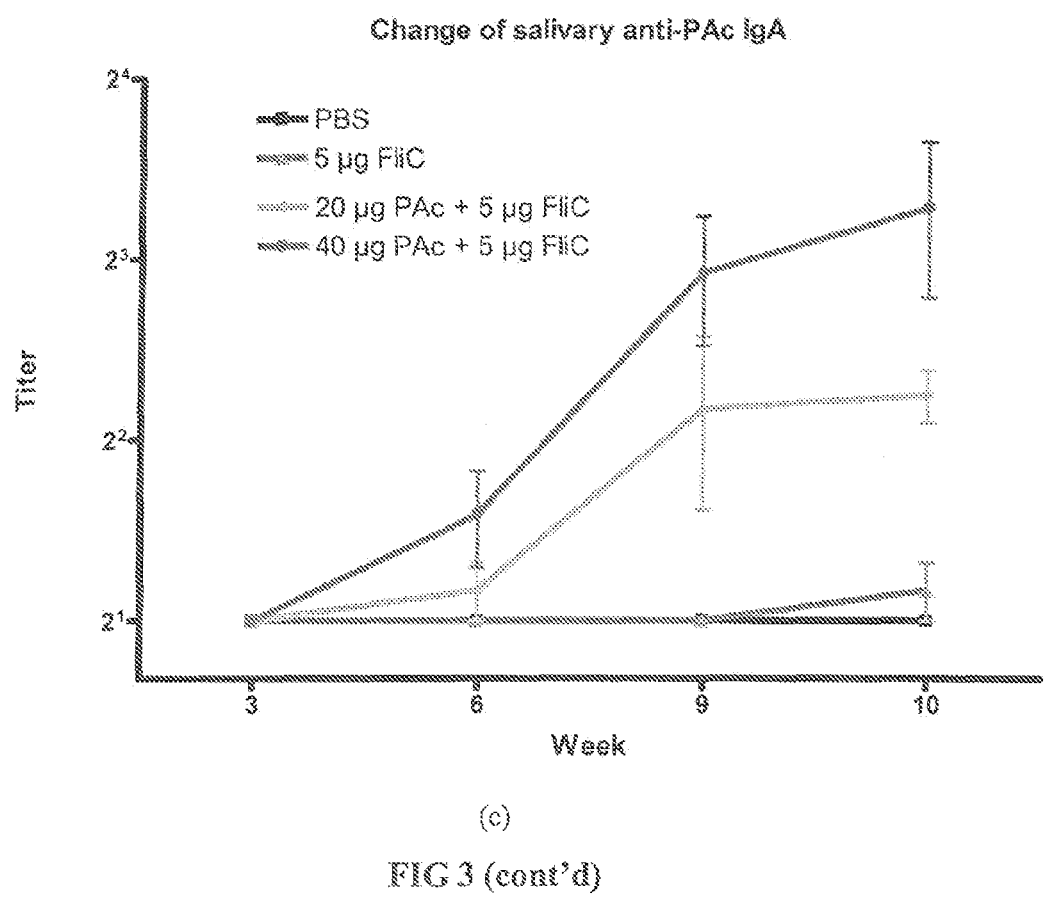

Referring to FIG. 3, there are provided graphs showing the titers of (a) serum anti-PAc IgG, (b) serum anti-PAc IgA, and (c) saliva anti-PAc IgA antibodies from four groups of rats intranasally immunized with: (1) PBS; (2) 5 μg FliC; (3) 20 μg PAc+5 μg FliC; (4) 40 μg PAc+5 μg FliC, where the data are expressed as means±standard deviation. The results from the rats were in line with the ones from the mice, showing that FliC was a potent enhancer for augmenting the anti-PAc antibody titers in the sera and saliva, and more importantly, in the presence of FliC, PAc was capable of inducing high level of specific anti-PAc IgG and IgA antibodies in both sera and saliva.

Figure 4:
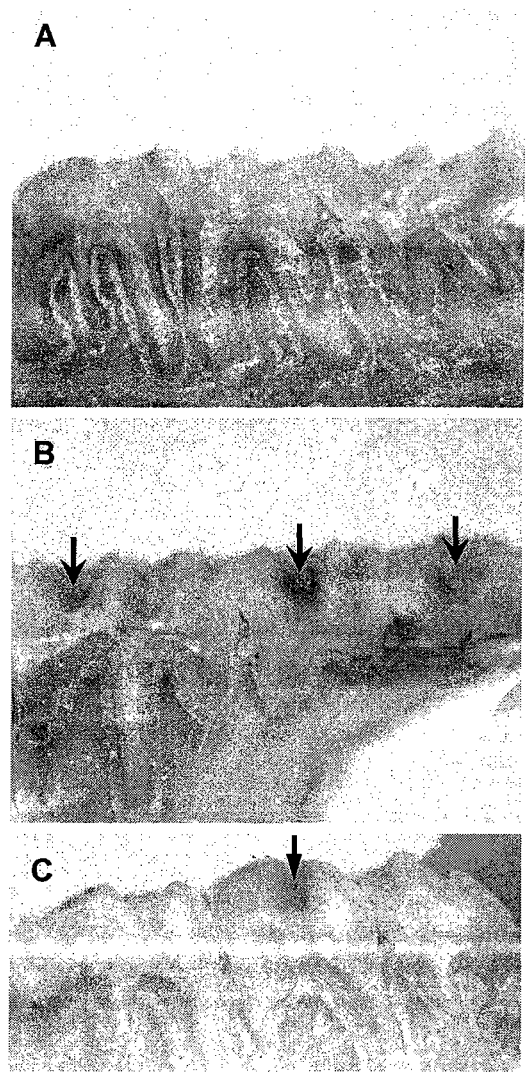
FIG. 4 shows three exemplary pictures illustrating (A) median-sagittal section of normal molar teeth of rat (right maxillary part of lingual side) and (B) median-sagittal section of carious molar teeth of rat challenged and infected by *S. nutans* Ingbritt (right mandible part of lingual side), where dental caries of different levels are indicated by arrows in the pictures. (C) median-sagittal section of molar teeth of 20 μg PAc+5 μg FloC immunized rat subsequently challenged with *S. mutan* Ingbritt (right mandible part of lingual side). Mild carious spot could be observed sporadically and one was indicated by arrowhead.

Now referring to FIG. 4, there are provided exemplary pictures illustrating (a) median-sagittal section of normal molar teeth of rat (right maxillary part of lingual side), (b) median-sagittal section of carious molar teeth of rat infected by S. mutans Ingbritt (right mandible part of lingual side), where dental caries of different levels are indicated by arrows in the picture, and (c) median-sagittal section of carious molar teeth of rat immunized first with PAc and FliC composition and then infected by S. mutans Ingbritt (right mandible part of lingual side), where minor dental caries is indicated by an arrow in the picture. It was evident that the rat model was useful because artificial dental caries were induced in the infected rats.

Figure 5:
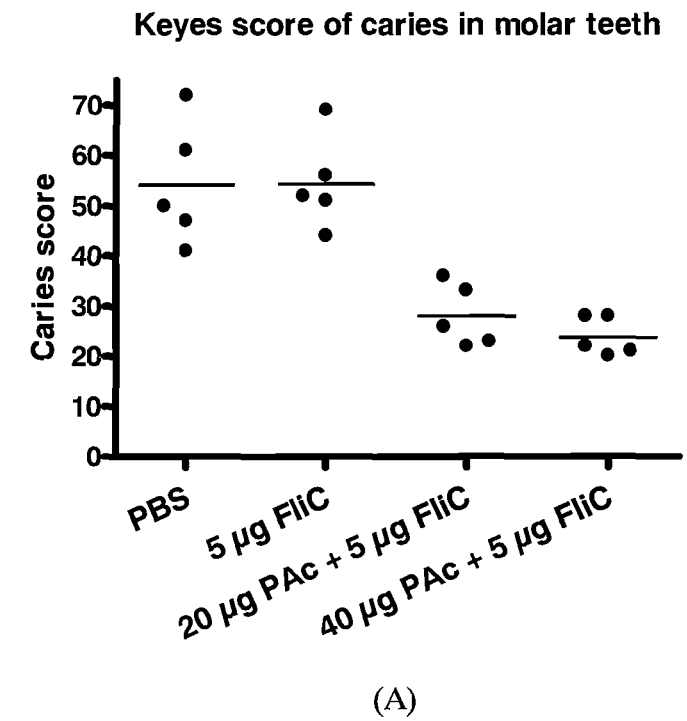
FIG. 5 contains two graphs showing (A) overall score of dental caries of four groups of rats, each dot represents carious level of each rat and (B) Keyes score of dental caries in different parts of molar teeth of four groups rats intranasally immunized with: (1) PBS; (2) 5 μg FliC; (3) 20 μg PAc+5 μg FliC; (4) 40 μg PAc+5 μg FliC. Values are expressed as the means plus standard deviations. *Significantly different from negative control group (p<0.05). Significantly different from negative control group (p<0.01). *Significantly different from negative control group (p<0.001). Symbols: , Enamel lesion; , Slight dentinal lesion; , Moderate dentinal lesion.
Figure 5:
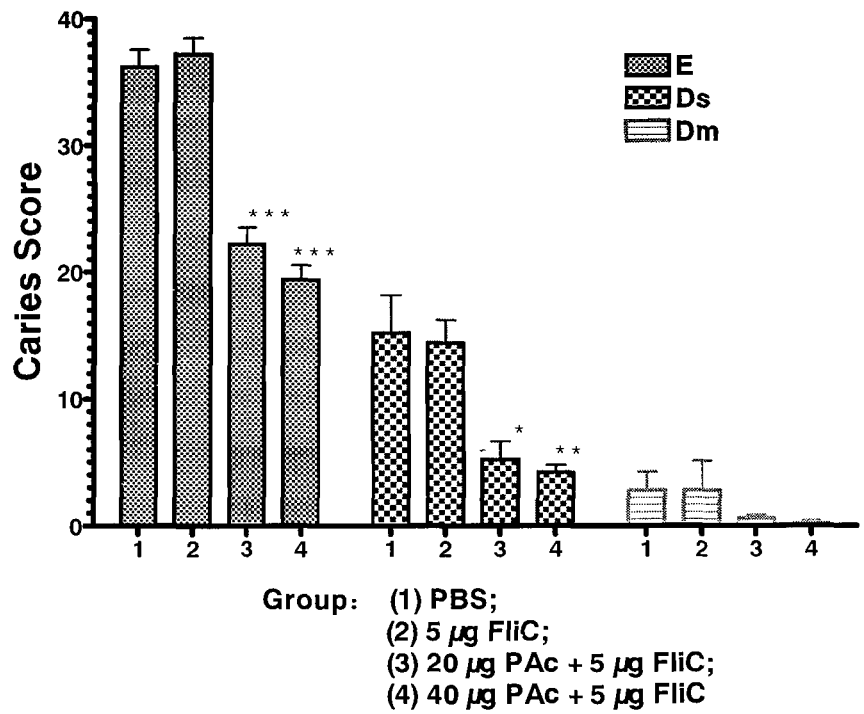

Now referring to FIG. 5, there are provided two graphs showing (A) overall score of dental caries of four groups of rats, each dot represents carious level of each rat and (B) Keyes score of dental caries in different parts of molar teeth of four groups rats intranasally immunized with: (1) PBS; (2) 5 μg FliC; (3) 20 μg PAc+5 μg FliC; (4) 40 μg PAc+5 μg FliC. Values are expressed as the means plus standard deviations. *Significantly different from negative control group (p<0.05). Significantly different from negative control group (p<0.01). *Significantly different from negative control group (p<0.001). Symbols: , Enamel lesion; , Slight dentinal lesion; , Moderate dentinal lesion.

As for overall carious lesions (FIG. 5A), rats of group 3 and 4 immunized via intranasal routes had fewer lesions than those of group 1 and 2. There are significant differences between group 4 and group 1 ($p<0.01$), group 4 and group 2 ($p<0.001$), group 5 and group 1 ($p<0.001$), group 5 and group 2 ($p<0.001$). The rats immunized with 40 μg PAc and 5 μg FliC through intranasal routes showed the least lesions. With regard to enamel, superficial dentinal, moderate dentinal lesions, there are also significant differences (FIG. 5B). As for enamel lesions (E), there are significant differences between group 4 and group 1 ($p<0.001$), group 4 and group 2 ($p<0.001$), group 5 and group 1 ($p<0.001$), group 5 and group 2 ($p<0.001$); for superficial dentinal lesions (Ds), there are significant differences between group 4 and group 1 ($p<0.05$), group 4 and group 2 ($p<0.01$), group 5 and group 1 ($p<0.01$), group 5 and group 2 ($p<0.001$). Due to low carious score for moderate dentinal lesions, there is no statistically significant difference between these groups, but we still can see less mean score for group 4 and group 5 compared with the former three groups.

The average carious scores of group 1, 2, 3, and 4 are 54.2, 54.4, 28 and 23.8 respectively. Therefore, rats of group 4 and 5 had 48% and 56% reductions respectively.

EXAMPLE 8

Construction of pET28a-KF-PAc Plasmid

Figure 6:
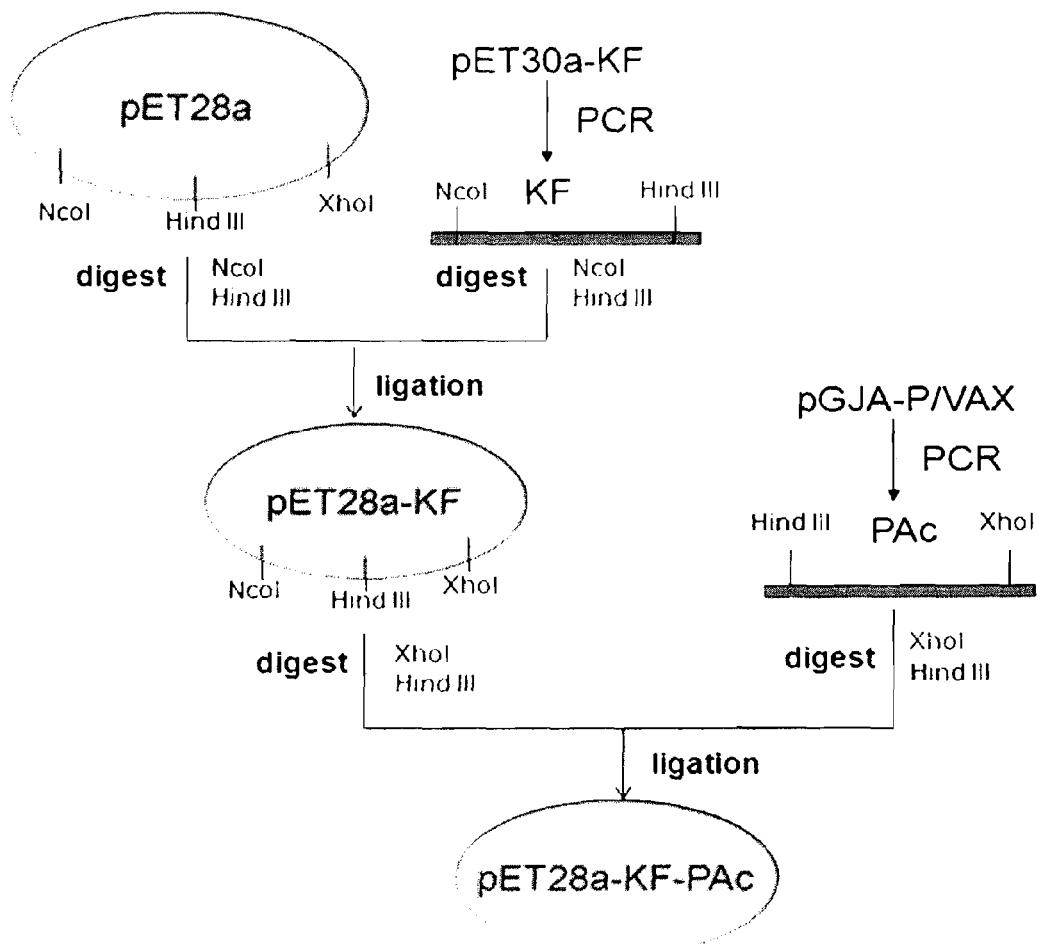
FIG. 6 illustrates the construction of pET28a-KF-PAc plasmid.

KF-PAc nucleotide sequence (SEQ ID NO 5) and amino acid sequence (SEQ ID NO 6), where KF denotes the flagellin derived from *E. coli* (SEQ ID NO 15 denotes KF nucleotide sequence, SEQ ID NO 16 denotes KF amino acid sequence). First, amplified KF and PAc fragments by PCR, where the up-stream primer for KF is 5' GCGCCATG GCACAAGT-CATTAATACC 3' (SEQ ID NO 7), the down-strem primer for KF is 5' AACAAGCTTACCCTGCAGCAGAGACAGAAC 3' (SEQ ID NO 8), and up- and down-stream primers were introduced Nco I or Hind III enzymatic sites respectively (the enzymatic sites are highlighted); the up-stream primer for PAc is 5' TCAAAGCTTGGAACCAATGCTGCCAATC 3' (SEQ ID NO 9), the down-stream primer for PAc is 5' ACGTCTCGAGCTCATAAGTTGGCTCAACAG 3' (SEQ ID NO 10), the up- and down-stream primers were introduced Hind III or Xho I enzymatic sites respectively. pET28a was chosen as the vector; ligated these two fragments sequentially into the vector; the resultant ligated product was used to transform BL21(DE3)star; picked positive clones for verification by enzymatic digestion and sequencing. The correct recombinant plasmid was designated as pET28a-KF-PAc; the expression product KF-PAc contained a (His)$_6$ tag at its C-terminal. The plasmid construction is illustrated in FIG. 6, where KF fragment contained 1494 bases encoding 498 amino acids (1-498), PAc fragment contained 2085 bases encoding 695 amino acids (501-1195); KF and PAc fragments were connected by 2 amino acids.

EXAMPLE 9

Construction of pET28a-KFD2-PAc Plasmid

Figure 7:
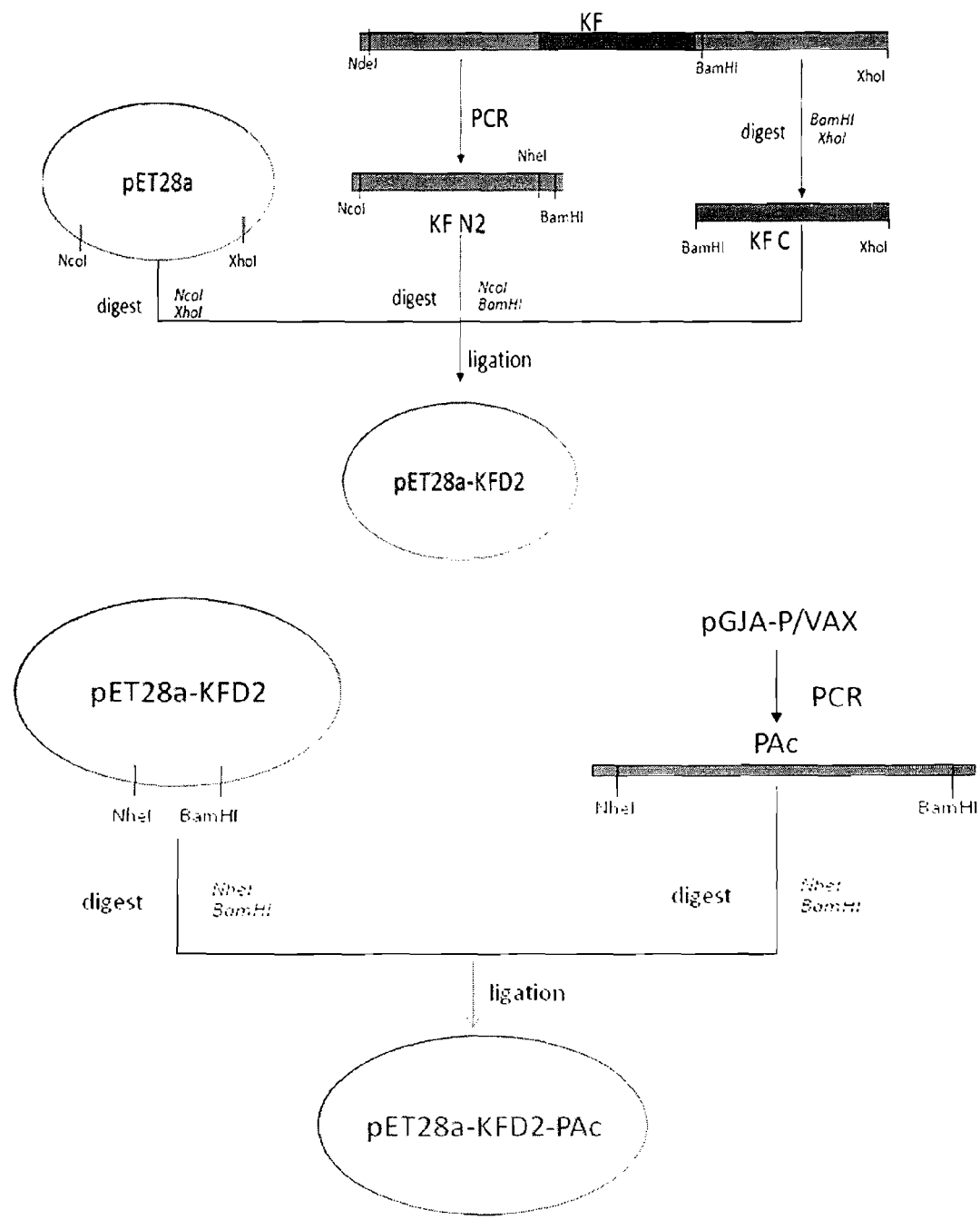
FIG. 7 illustrates the construction of pET28-KFD2-PAc plasmid.

KFD2-PAc nucleotide sequence (SEQ ID NO 11) and amino acid sequence (SEQ ID NO 12). First, amplified PAc fragment; the up-stream primer is 5' TATAGCTAGCGGA ACCAATGCTGCCAATC 3'(SEQ ID NO 13), the down-stream primer is 5' ATTAGGATCCGTCGTCTCATAAGT-TGGCTC 3' (SEQ ID NO 14); the up- and down-stream primers were introduced Nhe I or BamH I enzymatic sites respectively (the enzymatic sites are highlighted). Then ligated the fragment into the constructed pET28a-KFD2 plasmid; the ligated product was used to transform BL21(DE3) star; picked positive clones for verification by enzymatic digestion and sequencing. The correct recombinant plasmid was designated as pET28a-KFD2-PAc; the expression product KFD2-PAc contained a (His)$_6$ tag at its C-terminal. The plasmid construction is illustrated in FIG. 7, where PAc fragment contained 2061 bases encoding 687 amino acids (174-860).

Figure 8:
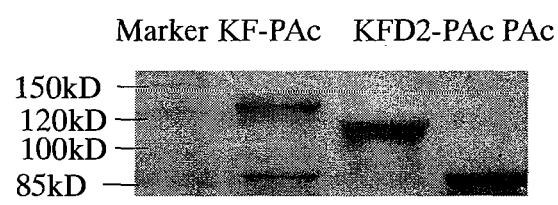
FIG. 8 shows the SDS-PAGE picture (A) and Western blot picture (B) of purified PAc, KF-PAc and KFD2-PAc.
Figure 8:
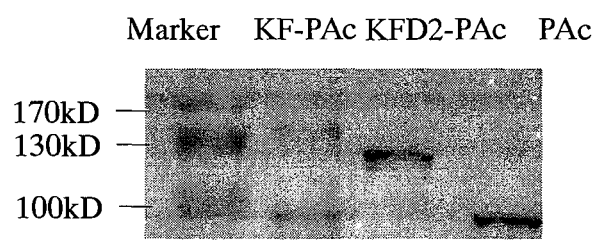

FIG. 8 shows the SDS-PAGE picture (A) and Western blot picture (B) of purified PAc, KF-PAc and KFD2-PAc.

EXAMPLE 10

Figure 9:
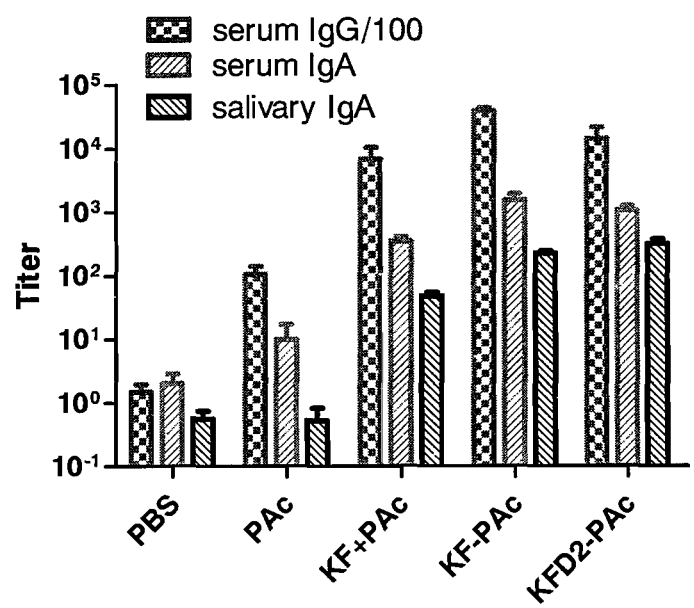
FIG. 9 is a graph showing serum anti-PAc IgG, serum anti-PAc IgA and saliva anti-PAc IgA titers in groups of mice immunized with PBS, PAc. KF+PAc, KF-PAc, or KFD2-PAc respectively, where the data are expressed as means±standard deviation.

Five groups of mice were intranasally immunized: (1) PBS; (2) 1 μg PAc; (3) 1 μg PAc+0.7 μg KF; (4) 1.7 μg KF-PAc; (5) 1.4 μg KFD2-PAc. After trice immunization, antibodies were analyzed as in Example 4. FIG. 9 is a graph showing serum anti-PAc IgG, serum anti-PAc IgA and saliva anti-PAc IgA titers, where the data are expressed as means±standard deviation.

EXAMPLE 11

Figure 10:
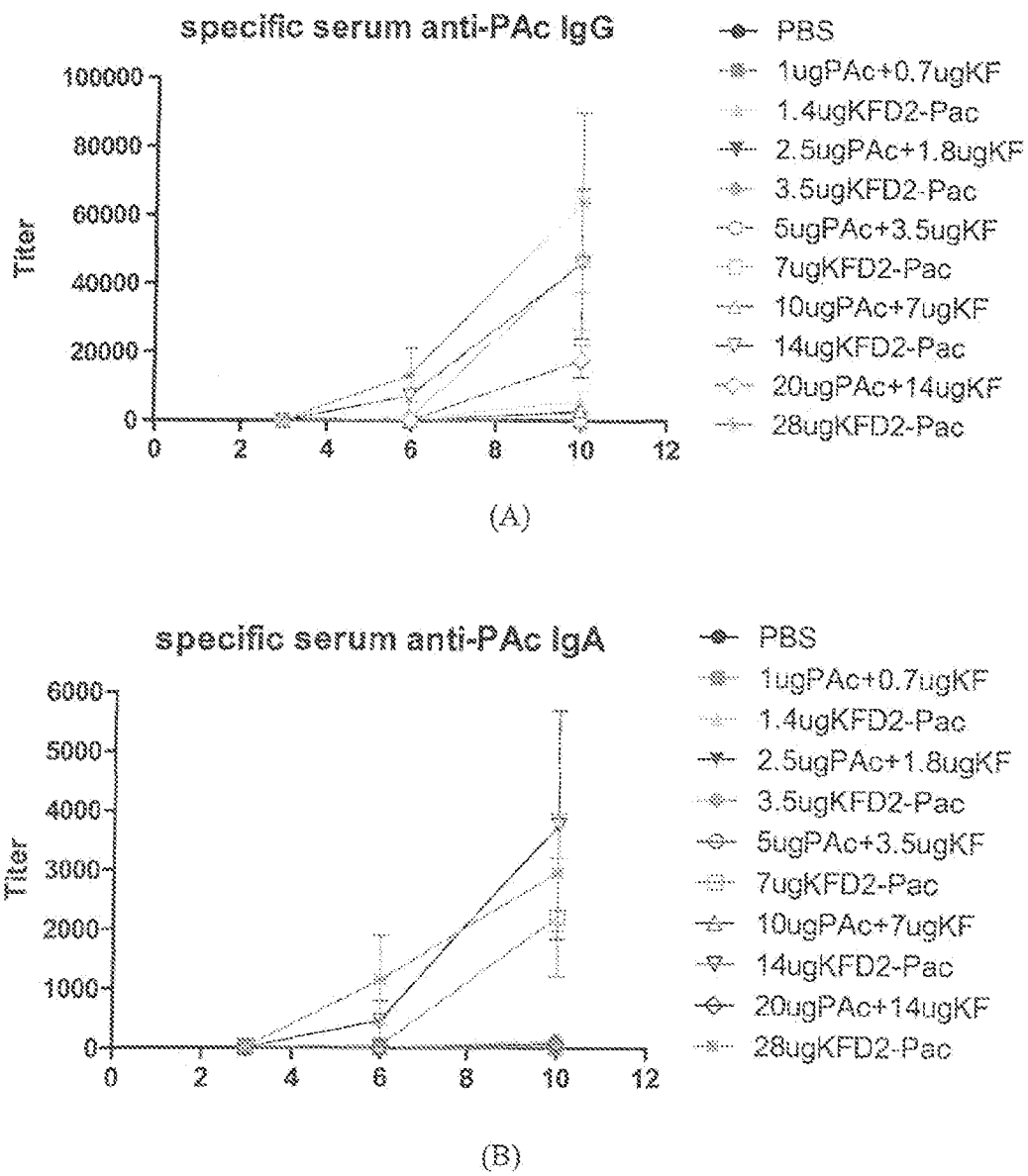
FIG. 10 includes three graphs showing (A) serum anti-PAc IgG, (B) serum anti-PAc IgA and (C) saliva anti-PAc IgA titers in groups of mice immunized with PBS, 1 ugPAc+0.7 ugKF, 1.4 ugKFD2-Pac, 2.5 ugPAc+1.8 ugKF, 3.5 ugKFD2-Pac, 5 ugPAc+3.5 ugKF, 7 ugKFD2-Pac, 10 ugPAc+7 ugKF, 14 ugKFD2-Pac, 20 ugPAc+14 ugKF, or 28 ugKFD2-Pac respectively, where the data are expressed as means±standard deviation.
Figure 10:
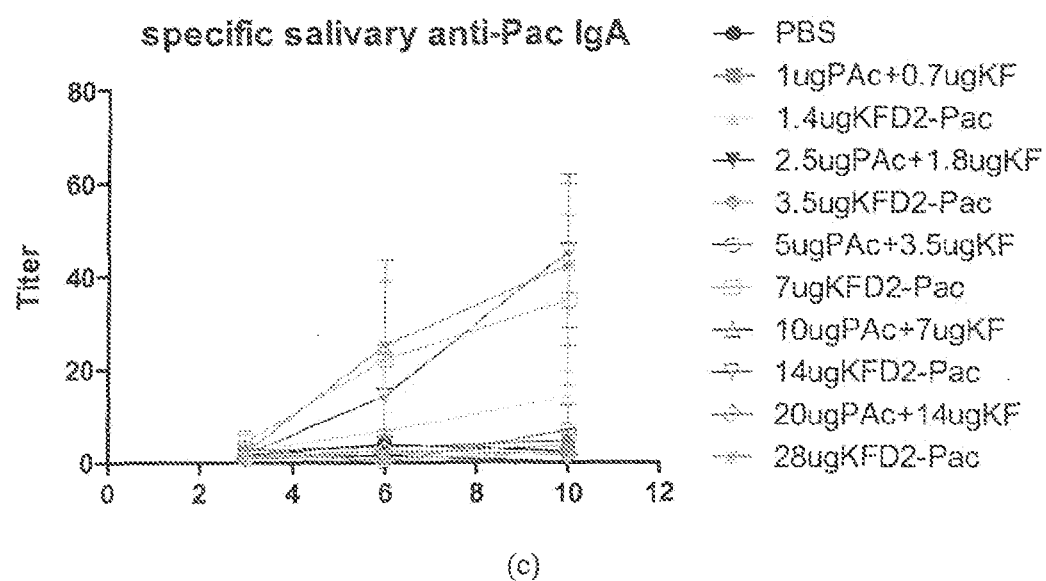

Eleven groups of rats were intranasally immunized: (1) PBS; (2) 1 μg PAc+0.7 μg KF; (3) 1.4 μg KFD2-PAc; (4) 2.5 μg PAc+1.8 μg KF; (5) 3.5 μg KFD2-PAc; (6) 5 μg PAc+3.5 μg KF; (7) 7 μg KFD2-PAc; (8) 10 μg PAc+7 μg KF; (9) 14 μg KFD2-PAc; (10) 20 μg PAc+14 μg KF; (11) 28 μg KFD2-PAc. After trice immunization, antibodies were analyzed as in Example 4. FIG. 10 includes three graphs showing (A) serum anti-PAc IgG, (B) serum anti-PAc IgA and (C) saliva anti-PAc IgA titers, where the data are expressed as means±standard deviation.

EXAMPLE 12

Figure 11:
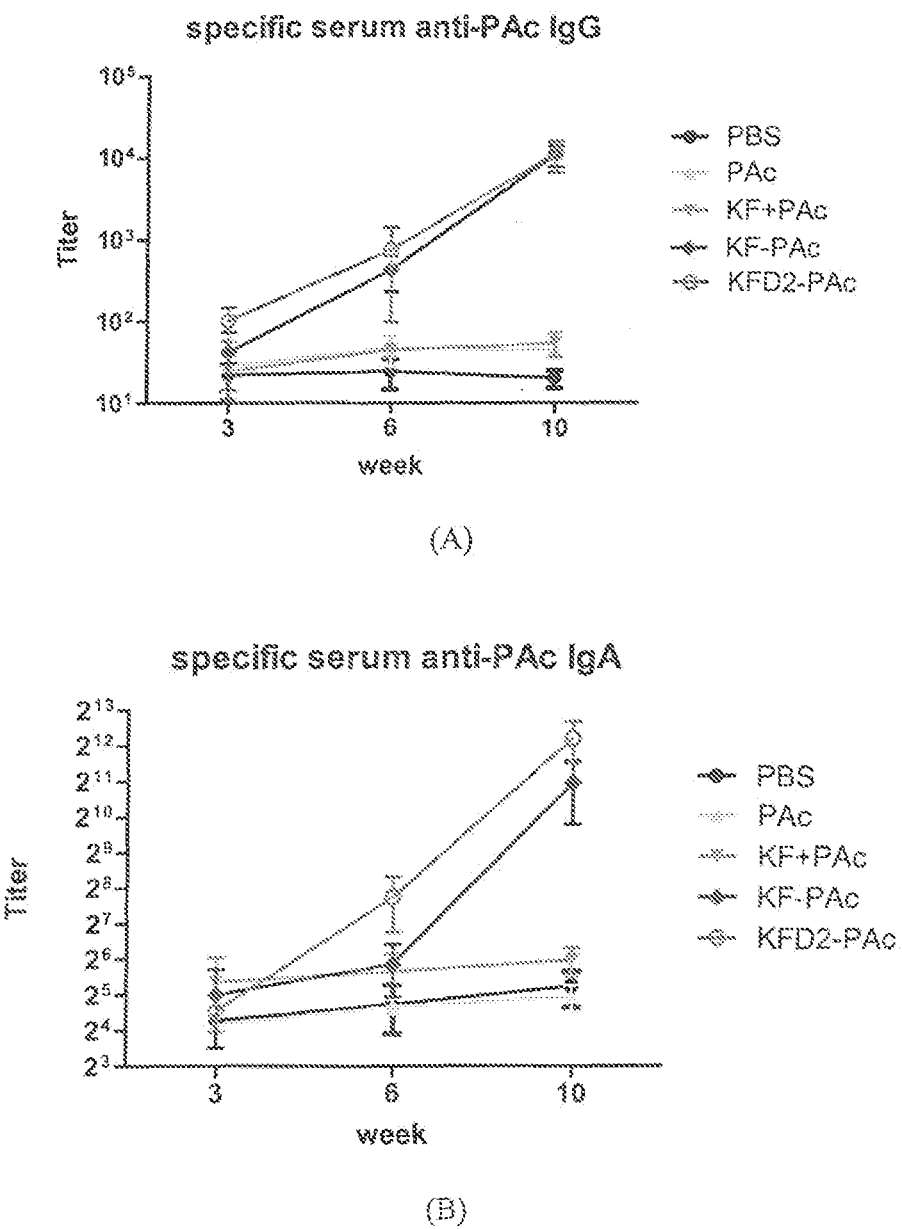
FIG. 11 includes three graphs showing (A) serum anti-PAc IgG, (B) serum anti-PAc IgA and (C) saliva anti-PAc IgA titers in groups of mice immunized with PBS, PAc, KF+PAc, KF-PAc, or KFD2-PAc respectively, where the data are expressed as means±standard deviation.
Figure 11:
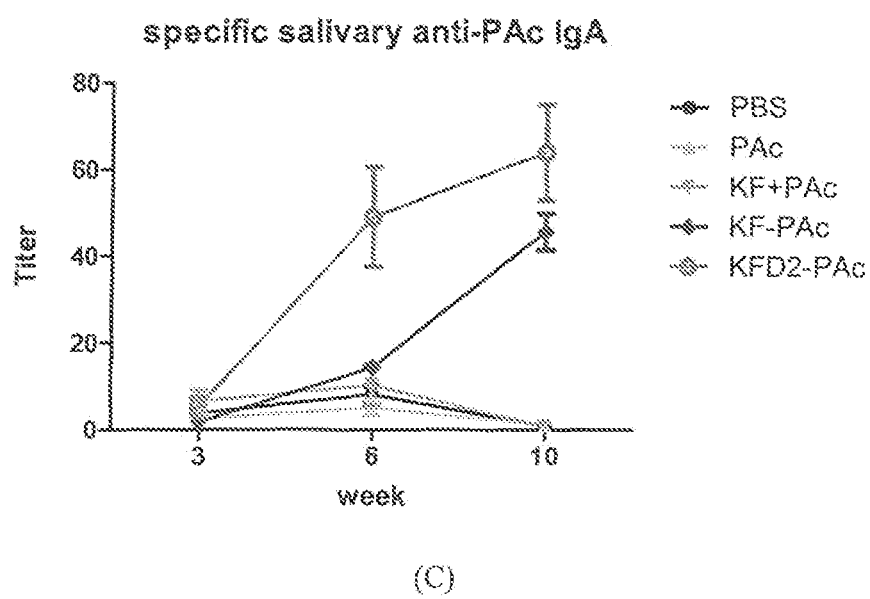

Five groups of rats were intranasally immunized: (1) PBS; (2) 5 μg PAc; (3) 5 μg PAc+3.5 μg KF; (4) 8.5 μg KF-PAc; (5) 7 μg KFD2-PAc. After trice immunization, antibodies were analyzed as in Example 4. FIG. 11 includes three graphs showing (A) serum anti-PAc IgG, (B) serum anti-PAc IgA and (C) saliva anti-PAc IgA titers, where the data are expressed as means±standard deviation.

EXAMPLE 13

Figure 12:
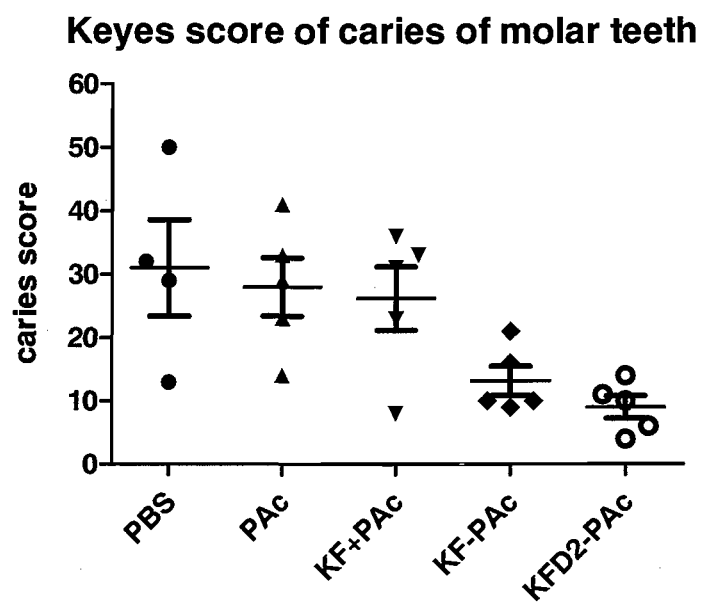
FIG. 12 is a graph showing the Keyes scores of five groups of rats immunized with PBS, PAc, KF-PAc, KF-PAc or KFD2-PAc respectively, each point represents the caries score of each rat, where the horizontal values are means±standard deviation.

Five groups of rats were intranasally immunized: (1) PBS; (2) 5 μg PAc; (3) 5 μg PAc+3.5 μg KF; (4) 8.5 μg KF-PAc; (5) 7 μg KFD2-PAc. The immunized rats were prior infected; the infection dose was $2 \times 10^9$ CFU. 12 weeks after infection, the scores were calculated, and carious teeth were analyzed as in Example 5. FIG. 12 is a graph showing the Keyes scores of five groups of rats, each point represents the caries score of each rat, where the horizontal values are means±standard deviation.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

What is claimed is:

1. A vaccine composition for dental caries caused by *S. mutans* infection, comprising:
   a PAc polypeptide encoded by SEQ ID NO 1 or a variant of the PAc polypeptide represented by SEQ ID NO 2;
   a flagellin polypeptide encoded by SEQ ID NO 3 or a variant of the flagellin represented by SEQ ID NO 4, wherein the flagellin polypeptide or flagellin variant contains a deletion in hypervariable domain of flagellin polypeptide; and
   a pharmaceutically acceptable carrier.

2. The vaccine composition of claim 1, wherein the PAc polypeptide or variant is a recombinant polypeptide conjoining at least two dispersed antigenic epitopes together.

3. The vaccine composition of claim 1, wherein the PAc and flagellin polypeptides are expressed as a single recombinant protein.

4. The vaccine composition of claim 3, wherein the single recombinant protein is encoded by SEQ ID NO 6.

5. The vaccine composition of claim 1, wherein the PAc polypeptide is inserted into the hypervariable domain of the flagellin polypeptide or substitutes partial or whole hypervariable domain of the flagellin polypeptide.

6. The vaccine composition of claim 5, wherein the PAc polypeptide is inserted into the hypervariable domain of the flagellin polypeptide to produce a PAc-flagellin polypeptide, and wherein the PAc-flagellin polypeptide is encoded by SEQ ID NO 12.

7. The vaccine composition of claim 1, wherein the PAc and flagellin polypeptides are tagged or conjugated with complementary moieties that bring these two molecules into close proximity.

8. The vaccine composition of claim 1, wherein the PAc and flagellin polypeptides are conjugated together.

9. The vaccine composition of claim 1, wherein the PAc and flagellin polypeptides are bound to a carrier that brings these two molecules into close proximity.

* * * * *

SEQUENCE LISTING

<160> NUMBER OF SEQ ID NOS: 16

<210> SEQ ID NO 1
<211> LENGTH: 4689
<212> TYPE: DNA
<213> ORGANISM: Streptococcus mutans

<400> SEQUENCE: 1

| | | | | | |
|---|---|---|---|---|---|
| atgaaagtca | aaaaaactta | cggttttcgt | aaaagtaaaa | ttagtaaaac | actgtgtggt | 60 |
| gctgttctag | aacagtagc | agcagtctct | gtagcaggac | aaaaggtttt | tgccgatgaa | 120 |
| acgaccacta | ctagtgatgt | agatactaaa | gtagttggga | cacaaactgg | aaatccagcg | 180 |
| accaatttgc | cagaggctca | agggagtgcg | agtaaggaag | ctgaacaaag | tcaaaaccaa | 240 |
| gctggagaga | caaatggttc | aataccagtt | gaagtaccta | aaactgatct | tgatcaagca | 300 |
| gcaaaagatg | ctaagtctgc | tggtgtcaat | gttgtccaag | atgctgatgt | taataaagga | 360 |
| actgttaaaa | cagctgaaga | agcagtccaa | aagaaactg | aaattaaaga | agattacaca | 420 |
| aaacaagctg | aggatattaa | gaagacaaca | gatcaatata | atcggatgt | agctgctcat | 480 |
| gaggcagaag | ttgctaaaat | taagctaaa | atcaggcaa | ctaaagaaca | gtatgaaaaa | 540 |
| gatatggcag | ctcataaagc | cgaggttgaa | cgcattaatg | ctgcaaatgc | tgccagtaaa | 600 |
| acagcttatg | aatctaaatt | ggctcaatat | caagtagatt | tagcagccgt | tcaaaaaacc | 660 |
| aatgctgcca | atcaagcagc | ctatcaaaaa | gcccttgctg | cttatcaggc | tgaactgaaa | 720 |
| cgtgttcagg | aagctaatgc | agccgccaaa | gccgcttatg | tatctgctgt | agcagcaaat | 780 |
| aatgccaaaa | atacagaaat | tgccgctgcc | aatgaagaaa | ttagaaaacg | caatgcaacg | 840 |
| gccaaagctg | aatatgagac | taagttagct | caatatcaag | ctgaactaaa | gcgtgttcag | 900 |
| gaagctaatg | ccgcaaacga | agcagactat | caagctaaat | tgaccgccta | tcaaacagag | 960 |
| cttgctcgcg | ttcaaaaggc | taatgcggat | gctaaagcgg | cctatgaagc | agctgtagca | 1020 |
| gcaaataatg | ccaaaaatgc | ggcactcaca | gctgaaaata | ctgcaattaa | gcaacgcaat | 1080 |
| gagaatgcta | aggcgactta | tgaagctgca | ctcaagcaat | atgaggccga | tttggcaacg | 1140 |
| gtgaaaaaag | ctaatgccgc | aaacgaagca | gactatcaag | ctaaattgac | cgcctatcaa | 1200 |
| acagagctcg | ctcgcgttca | aaaagccaat | gcggatgcta | aagcggccta | tgaagcagct | 1260 |
| gtagcagcaa | ataatgccgc | aaatgcagcg | ctcacagctg | aaaatactgc | aattaagaag | 1320 |
| cgcaatgcgg | atgctaaagc | tgattacgaa | gcaaaacttg | ctaagtatca | agcagatctt | 1380 |
| gccaaatatc | aaaaagattt | agcagactat | ccagttaagt | taaaggcata | cgaagatgaa | 1440 |
| caagcttcta | ttaagctgc | actggcagaa | cttgaaaaac | ataaaaatga | agacggaaac | 1500 |
| ttaacagaac | catctgctca | aaatttggtc | tatgatcttg | agccaaatgc | gaacttatct | 1560 |
| ttgacaacag | atgggaagtt | ccttaaggct | tctgctgtgg | atgatgcttt | tagcaaaagc | 1620 |
| acttcaaaag | caaatatga | ccaaaaaatt | cttcaattag | atgatctaga | tatcactaac | 1680 |
| ttagaacaat | ctaatgatgt | tgcttcttct | atggagcttt | atgggaattt | tggtgataaa | 1740 |
| gctggctggt | caacgacagt | aagcaataac | tcacaggtta | aatggggatc | ggtacttta | 1800 |
| gagcgcggtc | aaagcgcaac | agctacatac | actaacctgc | agaattctta | ttacaatggt | 1860 |
| aaaaagattt | ctaaaattgt | ctacaagtat | acagtggacc | ctaagtccaa | gtttcaaggt | 1920 |
| caaaaggttt | ggttaggtat | ttttaccgat | ccaactttag | gtgttttgc | ttccgcttat | 1980 |
| acaggtcaag | ttgaaaaaaa | cacttctatt | tttattaaaa | atgaatttac | tttctatgac | 2040 |
| gaagatggaa | aaccaattaa | ttttgataat | gcccttctct | cagtagcttc | tcttaaccgt | 2100 |

```
gaaaataatt ctattgagat ggctaaagat tatacgggta aatttgtcaa aatctctgga    2160
tcatctatcg gtgaaaagaa tggcatgatt tatgctacag atactctcaa ctttaggcag    2220
ggtcaaggtg gtgctcgttg gaccatgtat accagagcta gcgaaccggg atctggctgg    2280
gatagttcag atgcgcctaa ctcttggtat ggtgctggtg ctatccgcat gtctggtcct    2340
aataacagtg tgactttggg tgctatctca tcaacacttg ttgtgcctgc tgatcccaca    2400
atggcaattg aaactggcaa aaaccaaat atttggtatt ctttaaatgg taaaatccgt     2460
gcggttaatg ttcctaaagt tactaaggaa aaacccacac ctccggttaa accaacagct    2520
ccaactaaac caacttatga aacagaaaag ccattaaaac cggcaccagt agctccaaat    2580
tatgaaaagg agccaacacc gccgacaaga acaccgaatc aagcagagcc aaacaaaccc    2640
acaccgccga cctatgaaac agaaaagccg ttggagccag cacctgttga gccaagctat    2700
gaagcagagc caacaccgcc gacaaggaca ccggatcagg cagagccaaa taaacccaca    2760
ccgccgacct atgaaacaga aaagccgttg gagccagcac tgttgagcc aagctatgaa     2820 gcagagccaa cgccaccgac accaacacca gatcaaccag aaccaaacaa acctgttgag    2880
ccaacttatg aggttattcc aacaccgccg actgatcctg tttatcaaga tcttccaaca    2940
cctccatctg taccaactgt tcatttccat tactttaaac tagctgttca gccgcaggtt    3000
aacaaagaaa ttagaaacaa taacgatgtt aatattgaca gaacttttggt ggctaaacaa   3060 tctgttgtta agttccagct gaagacagca gatctccctg ctggacgtga tgaaacaact    3120
tcctttgtct tggtagatcc cctgccatct ggttatcaat ttaatcctga agctacaaaa    3180
gctgccagcc ctggctttga tgtcgcttat gataatgcaa ctaatacagt caccttcaag    3240
gcaactgcag caacttttggc tacgtttaat gctgatttga ctaaatcagt ggcaacgatt    3300
tatccaacag tggtcggaca agttcttaat gatggcgcaa cttataagaa taatttcacg    3360
ctcacagtca atgatgctta tggcattaaa tccaatgttg ttcgggtgac aactcctggt    3420
aaaccaaatg atccagataa cccaaataat aattatatta aaccaactaa ggttaataaa    3480
aacgaaaatg gcgttgttat tgatggtaaa acagttcttg ccggttcaac gaattattat    3540
gagctaactt gggatttgga tcaatataaa acgaccgct cttcagcaga taccattcaa    3600
aaaggatttt actatgtaga tgattatcca gaagaagcgc ttgaattgcg tcaggattta    3660
gtgaagatta cagatgctaa tggtaatgaa gttactggtg ttagtgtgga taattatact    3720
agtcttgaag cagcccctca agaaattaga gatgttcttt ctaaggcagg aattagacct    3780
aaaggtgctt tccaaatttt ccgtgccgat aatccaagag aattttatga tacttatgtc    3840
aaaactggaa ttgatttgaa gattgtatca ccaatggttg ttaaaaaaca aatgggacaa    3900
acaggcggca gttatgaaaa tcaagcttac caaattgact ttggtaatgg ttatgcatca    3960
aatatcgtta tcaataatgt tcctaagatt aaccctaaga agatgtgac cttaacactt    4020 gatccggctg atacaaataa tgttgatggt cagactattc cacttaatac agtctttaat    4080
taccgtttga ttggtggcat tatccctgca aatcactcag aagaactctt tgaatacaat    4140
ttctatgatg attatgatca aacaggagat cactatactg gtcagtataa agttttttgcc   4200 aaggttgata tcactttttaa agacggttct attatcaagt caggtgctga gttaactcag   4260
tatacgacag cggaagttga taccgctaaa ggtgctatca caattaagtt caaggaagcc    4320
tttctgcgtt ctgtttcaat tgattcagcc ttccaagctg aaagtatat ccaaatgaaa     4380 cgtattgcgg ttggtacttt tgaaaatact tatattaata ctgtcaatgg ggtaacttac    4440
```

-continued

```
agttcaaata cagtgaagac aactactcct gaggatccta cagaccctac tgatccgcaa    4500
gatccatcat caccgcggac ttcaactgta attaactata aacctcaatc aactgcttat    4560
caaccaagct ctgttcaaga acattacca aatacgggag taacaaacaa tgcttatatg    4620
cctttacttg gtattattgg cttagttact agttttagtt tgcttggttt aaaggctaag    4680
aaagattga                                                           4689
```

<210> SEQ ID NO 2
<211> LENGTH: 1562
<212> TYPE: PRT
<213> ORGANISM: Streptococcus mutans

<400> SEQUENCE: 2

```
Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Glu Ala Glu Gln Ser Gln Asn Gln
65                  70                  75                  80

Ala Gly Glu Thr Asn Gly Ser Ile Pro Val Glu Val Pro Lys Thr Asp
                85                  90                  95

Leu Asp Gln Ala Ala Lys Asp Ala Lys Ser Ala Gly Val Asn Val Val
            100                 105                 110

Gln Asp Ala Asp Val Asn Lys Gly Thr Val Lys Thr Ala Glu Glu Ala
        115                 120                 125

Val Gln Lys Glu Thr Glu Ile Lys Glu Asp Tyr Thr Lys Gln Ala Glu
    130                 135                 140

Asp Ile Lys Lys Thr Thr Asp Gln Tyr Lys Ser Asp Val Ala Ala His
145                 150                 155                 160

Glu Ala Glu Val Ala Lys Ile Lys Ala Lys Asn Gln Ala Thr Lys Glu
                165                 170                 175

Gln Tyr Glu Lys Asp Met Ala Ala His Lys Ala Glu Val Glu Arg Ile
            180                 185                 190

Asn Ala Ala Asn Ala Ala Ser Lys Thr Ala Tyr Glu Ser Lys Leu Ala
        195                 200                 205

Gln Tyr Gln Val Asp Leu Ala Ala Val Gln Lys Thr Asn Ala Ala Asn
    210                 215                 220

Gln Ala Ala Tyr Gln Lys Ala Leu Ala Ala Tyr Gln Ala Glu Leu Lys
225                 230                 235                 240

Arg Val Gln Glu Ala Asn Ala Ala Lys Ala Ala Tyr Asp Thr Ala
                245                 250                 255

Val Ala Ala Asn Asn Ala Lys Asn Thr Glu Ile Ala Ala Ala Asn Glu
            260                 265                 270

Glu Ile Arg Lys Arg Asn Ala Thr Lys Ala Glu Tyr Glu Thr Lys
        275                 280                 285

Leu Ala Gln Tyr Gln Ala Glu Leu Lys Arg Val Glu Ala Asn Ala
    290                 295                 300

Ala Asn Glu Ala Asp Tyr Gln Ala Lys Leu Thr Ala Tyr Gln Thr Glu
305                 310                 315                 320

Leu Ala Arg Val Gln Lys Ala Asn Ala Asp Ala Lys Ala Ala Tyr Glu
```

```
                   325                 330                 335
Ala Ala Val Ala Ala Asn Asn Ala Lys Asn Ala Ala Leu Thr Ala Glu
            340                 345                 350

Asn Thr Ala Ile Lys Gln Arg Asn Glu Asn Ala Lys Ala Thr Tyr Glu
            355                 360                 365

Ala Ala Leu Lys Gln Tyr Glu Ala Asp Leu Ala Thr Val Lys Lys Ala
            370                 375                 380

Asn Ala Ala Asn Glu Ala Asp Tyr Gln Ala Lys Leu Thr Ala Tyr Gln
385                 390                 395                 400

Thr Glu Leu Ala Arg Val Gln Lys Ala Asn Ala Asp Ala Lys Ala Ala
            405                 410                 415

Tyr Glu Ala Ala Val Ala Ala Asn Asn Ala Asn Ala Ala Leu Thr
            420                 425                 430

Ala Glu Asn Thr Ala Ile Lys Lys Arg Asn Ala Asp Ala Lys Ala Asp
            435                 440                 445

Tyr Glu Ala Lys Leu Ala Lys Tyr Gln Ala Asp Leu Ala Lys Tyr Gln
            450                 455                 460

Lys Asp Leu Ala Asp Tyr Pro Val Lys Leu Lys Ala Tyr Glu Asp Glu
465                 470                 475                 480

Gln Ala Ser Ile Lys Ala Ala Leu Ala Glu Leu Lys His Lys Asn
            485                 490                 495

Glu Asp Gly Asn Leu Thr Glu Pro Ser Ala Gln Asn Leu Val Tyr Asp
            500                 505                 510

Leu Glu Pro Asn Ala Asn Leu Ser Leu Thr Thr Asp Gly Lys Phe Leu
            515                 520                 525

Lys Ala Ser Ala Val Asp Asp Ala Phe Ser Lys Ser Thr Ser Lys Ala
            530                 535                 540

Lys Tyr Asp Gln Lys Ile Leu Gln Leu Asp Leu Asp Ile Thr Asn
545                 550                 555                 560

Leu Glu Gln Ser Asn Asp Val Ala Ser Ser Met Glu Leu Tyr Gly Asn
            565                 570                 575

Phe Gly Asp Lys Ala Gly Trp Ser Thr Thr Val Ser Asn Asn Ser Gln
            580                 585                 590

Val Lys Trp Gly Ser Val Leu Leu Glu Arg Gly Gln Ser Ala Thr Ala
            595                 600                 605

Thr Tyr Thr Asn Leu Gln Asn Ser Tyr Tyr Asn Gly Lys Lys Ile Ser
            610                 615                 620

Lys Ile Val Tyr Lys Tyr Thr Val Asp Pro Lys Ser Lys Phe Gln Gly
625                 630                 635                 640

Gln Lys Val Trp Leu Gly Ile Phe Thr Asp Pro Thr Leu Gly Val Phe
            645                 650                 655

Ala Ser Ala Tyr Thr Gly Gln Val Glu Lys Asn Thr Ser Ile Phe Ile
            660                 665                 670

Lys Asn Glu Phe Thr Phe Tyr Asp Glu Asp Gly Lys Pro Ile Asn Phe
            675                 680                 685

Asp Asn Ala Leu Leu Ser Val Ala Ser Leu Asn Arg Glu Asn Asn Ser
            690                 695                 700

Ile Glu Met Ala Lys Asp Tyr Thr Gly Lys Phe Val Lys Ile Ser Gly
705                 710                 715                 720

Ser Ser Ile Gly Glu Lys Asn Gly Met Ile Tyr Ala Thr Asp Thr Leu
            725                 730                 735

Asn Phe Arg Gln Gly Gln Gly Gly Ala Arg Trp Thr Met Tyr Thr Arg
            740                 745                 750
```

-continued

```
Ala Ser Glu Pro Gly Ser Gly Trp Asp Ser Asp Ala Pro Asn Ser
        755                 760                 765

Trp Tyr Gly Ala Gly Ala Ile Arg Met Ser Gly Pro Asn Asn Ser Val
        770                 775                 780

Thr Leu Gly Ala Ile Ser Ser Thr Leu Val Val Pro Ala Asp Pro Thr
785                 790                 795                 800

Met Ala Ile Glu Thr Gly Lys Lys Pro Asn Ile Trp Tyr Ser Leu Asn
                805                 810                 815

Gly Lys Ile Arg Ala Val Asn Val Pro Lys Val Thr Lys Glu Lys Pro
                820                 825                 830

Thr Pro Pro Val Lys Pro Thr Ala Pro Thr Lys Pro Thr Tyr Glu Thr
                835                 840                 845

Glu Lys Pro Leu Lys Pro Ala Pro Val Ala Pro Asn Tyr Glu Lys Glu
        850                 855                 860

Pro Thr Pro Pro Thr Arg Thr Pro Asn Gln Ala Glu Pro Asn Lys Pro
865                 870                 875                 880

Thr Pro Pro Thr Tyr Glu Thr Glu Lys Pro Leu Glu Pro Ala Pro Val
                885                 890                 895

Glu Pro Ser Tyr Glu Ala Glu Pro Thr Pro Pro Thr Arg Thr Pro Asp
        900                 905                 910

Gln Ala Glu Pro Asn Lys Pro Thr Pro Pro Thr Tyr Glu Thr Glu Lys
                915                 920                 925

Pro Leu Glu Pro Ala Pro Val Glu Pro Ser Tyr Glu Ala Glu Pro Thr
        930                 935                 940

Pro Pro Thr Pro Thr Pro Asp Gln Pro Glu Pro Asn Lys Pro Val Glu
945                 950                 955                 960

Pro Thr Tyr Glu Val Ile Pro Thr Pro Pro Thr Asp Pro Val Tyr Gln
                965                 970                 975

Asp Leu Pro Thr Pro Pro Ser Val Pro Thr Val His Phe His Tyr Phe
                980                 985                 990

Lys Leu Ala Val Gln Pro Gln Val Asn Lys Glu Ile Arg Asn Asn Asn
        995                 1000                1005

Asp Val Asn Ile Asp Arg Thr Leu Val Ala Lys Gln Ser Val Val
        1010                1015                1020

Lys Phe Gln Leu Lys Thr Ala Asp Leu Pro Ala Gly Arg Asp Glu
        1025                1030                1035

Thr Thr Ser Phe Val Leu Val Asp Pro Leu Pro Ser Gly Tyr Gln
        1040                1045                1050

Phe Asn Pro Glu Ala Thr Lys Ala Ala Ser Pro Gly Phe Asp Val
        1055                1060                1065

Ala Tyr Asp Asn Ala Thr Asn Thr Val Thr Phe Lys Ala Thr Ala
        1070                1075                1080

Ala Thr Leu Ala Thr Phe Asn Ala Asp Leu Thr Lys Ser Val Ala
        1085                1090                1095

Thr Ile Tyr Pro Thr Val Val Gly Gln Val Leu Asn Asp Gly Ala
        1100                1105                1110

Thr Tyr Lys Asn Asn Phe Thr Leu Thr Val Asn Asp Ala Tyr Gly
        1115                1120                1125

Ile Lys Ser Asn Val Val Arg Val Thr Pro Gly Lys Pro Asn
        1130                1135                1140

Asp Pro Asp Asn Pro Asn Asn Asn Tyr Ile Lys Pro Thr Lys Val
        1145                1150                1155
```

```
Asn Lys Asn Glu Asn Gly Val Val Ile Asp Gly Lys Thr Val Leu
    1160            1165                1170
Ala Gly Ser Thr Asn Tyr Tyr Glu Leu Thr Trp Asp Leu Asp Gln
    1175            1180                1185
Tyr Lys Asn Asp Arg Ser Ser Ala Asp Thr Ile Gln Lys Gly Phe
    1190            1195                1200
Tyr Tyr Val Asp Asp Tyr Pro Glu Glu Ala Leu Glu Leu Arg Gln
    1205            1210                1215
Asp Leu Val Lys Ile Thr Asp Ala Asn Gly Asn Glu Val Thr Gly
    1220            1225                1230
Val Ser Val Asp Asn Tyr Thr Ser Leu Glu Ala Ala Pro Gln Glu
    1235            1240                1245
Ile Arg Asp Val Leu Ser Lys Ala Gly Ile Arg Pro Lys Gly Ala
    1250            1255                1260
Phe Gln Ile Phe Arg Ala Asp Asn Pro Arg Glu Phe Tyr Asp Thr
    1265            1270                1275
Tyr Val Lys Thr Gly Ile Asp Leu Lys Ile Val Ser Pro Met Val
    1280            1285                1290
Val Lys Lys Gln Met Gly Gln Thr Gly Gly Ser Tyr Glu Asn Gln
    1295            1300                1305
Ala Tyr Gln Ile Asp Phe Gly Asn Gly Tyr Ala Ser Asn Ile Val
    1310            1315                1320
Ile Asn Asn Val Pro Lys Ile Asn Pro Lys Lys Asp Val Thr Leu
    1325            1330                1335
Thr Leu Asp Pro Ala Asp Thr Asn Asn Val Asp Gly Gln Thr Ile
    1340            1345                1350
Pro Leu Asn Thr Val Phe Asn Tyr Arg Leu Ile Gly Gly Ile Ile
    1355            1360                1365
Pro Ala Asn His Ser Glu Glu Leu Phe Glu Tyr Asn Phe Tyr Asp
    1370            1375                1380
Asp Tyr Asp Gln Thr Gly Asp His Tyr Thr Gly Gln Tyr Lys Val
    1385            1390                1395
Phe Ala Lys Val Asp Ile Thr Phe Lys Asp Gly Ser Ile Ile Lys
    1400            1405                1410
Ser Gly Ala Glu Leu Thr Gln Tyr Thr Thr Ala Glu Val Asp Thr
    1415            1420                1425
Ala Lys Gly Ala Ile Thr Ile Lys Phe Lys Glu Ala Phe Leu Arg
    1430            1435                1440
Ser Val Ser Ile Asp Ser Ala Phe Gln Ala Glu Ser Tyr Ile Gln
    1445            1450                1455
Met Lys Arg Ile Ala Val Gly Thr Phe Glu Asn Thr Tyr Ile Asn
    1460            1465                1470
Thr Val Asn Gly Val Thr Tyr Ser Ser Asn Thr Val Lys Thr Thr
    1475            1480                1485
Thr Pro Glu Asp Pro Thr Asp Pro Thr Asp Pro Gln Asp Pro Ser
    1490            1495                1500
Ser Pro Arg Thr Ser Thr Val Ile Asn Tyr Lys Pro Gln Ser Thr
    1505            1510                1515
Ala Tyr Gln Pro Ser Ser Val Gln Glu Thr Leu Pro Asn Thr Gly
    1520            1525                1530
Val Thr Asn Asn Ala Tyr Met Pro Leu Leu Gly Ile Ile Gly Leu
    1535            1540                1545
Val Thr Ser Phe Ser Leu Leu Gly Leu Lys Ala Lys Lys Asp
```

<210> SEQ ID NO 3
<211> LENGTH: 1521
<212> TYPE: DNA
<213> ORGANISM: Salmonella enterica
<300> PUBLICATION INFORMATION:
<308> DATABASE ACCESSION NUMBER: NC_004631.1
<309> DATABASE ENTRY DATE: 2010-05-12
<313> RELEVANT RESIDUES IN SEQ ID NO: (1)..(1521)

<400> SEQUENCE: 3

| | | | | | |
|---|---|---|---|---|---|
| atggcacaag | tcattaatac | aaacagcctg | tcgctgttga | cccagaataa | cctgaacaaa | 60 |
| tcccagtccg | cactgggcac | tgctatcgag | cgtttgtctt | ccggtctgcg | tatcaacagc | 120 |
| gcgaaagacg | atgcggcagg | acaggcgatt | gctaaccgtt | ttaccgcgaa | catcaaaggt | 180 |
| ctgactcagg | cttcccgtaa | cgctaacgac | ggtatctcca | ttgcgcagac | cactgaaggc | 240 |
| gcgctgaacg | aaatcaacaa | caacctgcag | cgtgtgcgtg | aactggcggt | tcagtctgcg | 300 |
| aatggtacta | actcccagtc | tgacctcgac | tccatccagg | ctgaaatcac | ccagcgcctg | 360 |
| aacgaaatcg | accgtgtatc | cggccagact | cagttcaacg | gcgtgaaagt | cctggcgcag | 420 |
| gacaacaccc | tgaccatcca | ggttggtgcc | aacgacggtg | aaactatcga | tattgattta | 480 |
| aaagaaatca | gctctaaaac | actgggactt | gataagctta | atgtccaaga | tgcctacacc | 540 |
| ccgaaagaaa | ctgctgtaac | cgttgataaa | actacctata | aaaatggtac | agatcctatt | 600 |
| acagcccaga | gcaatactga | tatccaaact | gcaattggcg | gtggtgcaac | ggggggttact | 660 |
| ggggctgata | tcaaatttaa | agatggtcaa | tactatttag | atgttaaagg | cggtgcttct | 720 |
| gctggtgttt | ataaagccac | ttatgatgaa | actacaaaga | aagttaatat | tgatacgact | 780 |
| gataaaactc | cgttggcaac | tgcggaagct | acagctattc | ggggaacggc | cactataacc | 840 |
| cacaaccaaa | ttgctgaagt | aacaaaagag | ggtgttgata | cgaccacagt | tgcggctcaa | 900 |
| cttgctgcag | caggggttac | tggcgccgat | aaggacaata | ctagccttgt | aaaactatcg | 960 |
| tttgaggata | aaaacggtaa | ggttattgat | ggtggctatg | cagtgaaaat | gggcgacgat | 1020 |
| ttctatgccg | ctacatatga | tgagaaaaca | ggtgcaatta | ctgctaaaac | cactacttat | 1080 |
| acagatggta | ctggcgttgc | tcaaactgga | gctgtgaaat | ttggtggcgc | aaatggtaaa | 1140 |
| tctgaagttg | ttactgctac | cgatggtaag | acttacttag | caagcgacct | tgacaaacat | 1200 |
| aacttcagaa | caggcggtga | gcttaaagag | gttaatacag | ataagactga | aaacccactg | 1260 |
| cagaaaattg | atgctgcctt | ggcacaggtt | gatacacttc | gttctgacct | gggtgcggtt | 1320 |
| cagaaccgtt | tcaactccgc | tatcaccaac | ctgggcaata | ccgtaaataa | cctgtcttct | 1380 |
| gcccgtagcc | gtatcgaaga | ttccgactac | gcaaccgaag | tctccaacat | gtctcgcgcg | 1440 |
| cagattctgc | agcaggccgg | tacctccgtt | ctggcgcagg | cgaaccaggt | tccgcaaaac | 1500 |
| gtcctctctt | tactgcgtta | a | | | | 1521 |

<210> SEQ ID NO 4
<211> LENGTH: 506
<212> TYPE: PRT
<213> ORGANISM: Salmonella enterica
<300> PUBLICATION INFORMATION:
<308> DATABASE ACCESSION NUMBER: GeneID/1070204
<309> DATABASE ENTRY DATE: 2010-05-12
<313> RELEVANT RESIDUES IN SEQ ID NO: (1)..(506)

<400> SEQUENCE: 4

Met Ala Gln Val Ile Asn Thr Asn Ser Leu Ser Leu Leu Thr Gln Asn

-continued

```
1               5                   10                  15
Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
                35                  40                  45

Ala Ile Ala Asn Arg Phe Thr Ala Asn Ile Lys Gly Leu Thr Gln Ala
            50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Gly Thr Asn Ser Gln Ser Asp Leu Asp Ser Ile
                100                 105                 110

Gln Ala Glu Ile Thr Gln Arg Leu Asn Glu Ile Asp Arg Val Ser Gly
                115                 120                 125

Gln Thr Gln Phe Asn Gly Val Lys Val Leu Ala Gln Asp Asn Thr Leu
                130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
                180                 185                 190

Tyr Lys Asn Gly Thr Asp Pro Ile Thr Ala Gln Ser Asn Thr Asp Ile
                195                 200                 205

Gln Thr Ala Ile Gly Gly Ala Thr Gly Val Thr Gly Ala Asp Ile
                210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
                260                 265                 270

Ile Arg Gly Thr Ala Thr Ile Thr His Asn Gln Ile Ala Glu Val Thr
                275                 280                 285

Lys Glu Gly Val Asp Thr Thr Val Ala Ala Gln Leu Ala Ala Ala
                290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Ala
                340                 345                 350

Ile Thr Ala Lys Thr Thr Thr Tyr Thr Asp Gly Thr Gly Val Ala Gln
                355                 360                 365

Thr Gly Ala Val Lys Phe Gly Gly Ala Asn Gly Lys Ser Glu Val Val
                370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
                420                 425                 430
```

```
Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Ser Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
            485                 490                 495

Val Pro Gln Asn Val Leu Ser Leu Leu Arg
        500                 505

<210> SEQ ID NO 5
<211> LENGTH: 3585
<212> TYPE: DNA
<213> ORGANISM: Artificial
<220> FEATURE:
<223> OTHER INFORMATION: KF-PAc fusion

<400> SEQUENCE: 5
```

| | | | | | |
|---|---|---|---|---|---|
| atggcacaag | tcattaatac | caacagcctc | tcgctgatca | ctcaaaataa | tatcaacaag | 60 |
| aaccagtctg | cgctgtcgag | ttctatcgag | cgtctgtctt | ctggcttgcg | tattaacagc | 120 |
| gcgaaggatg | acgcagcggg | tcaggcgatt | gctaaccgtt | tcacctctaa | cattaaaggc | 180 |
| ctgactcagg | cggcccgtaa | cgccaacgac | ggtatctccg | ttgcgcagac | caccgaaggc | 240 |
| gcgctgtccg | aaatcaacaa | caacttacag | cgtgtgcgtg | aactgacggt | acaggccact | 300 |
| accggtacta | actctgagtc | tgatctgtct | tctatccagg | acgaaattaa | atcccgtctg | 360 |
| gatgaaattg | accgcgtatc | tggtcagacc | cagttcaacg | gcgtgaacgt | gctggcaaaa | 420 |
| aatggctcca | tgaaaatcca | ggttggcgca | aatgataacc | agactatcac | tatcgatctg | 480 |
| aagcagattg | atgctaaaac | tcttggcctt | gatggtttta | gcgttaaaaa | taacgataca | 540 |
| gttaccacta | gtgctccagt | aactgctttt | ggtgctacca | ccacaaacaa | tattaaactt | 600 |
| actggaatta | ccctttctac | ggaagcagcc | actgatactg | gcggaactaa | cccagcttca | 660 |
| attgagggtg | tttatactga | taatggtaat | gattactatg | cgaaaatcac | cggtggtgat | 720 |
| aacgatggga | gtattacgc | agtaacagtt | gctaatgatg | gtacagtgac | aatggcgact | 780 |
| ggagcaacgg | caaatgcaac | tgtaactgat | gcaaatacta | ctaaagctac | aactatcact | 840 |
| tcaggcggta | cacctgttca | gattgataat | actgcaggtt | ccgcaactgc | caaccttggt | 900 |
| gctgttagct | agtaaaaact | gcaggattcc | aagggtaatg | ataccgatac | atatgcgctt | 960 |
| aaagatacaa | atggcaatct | ttacgctgcg | gatgtgaatg | aaactactgg | tgctgtttct | 1020 |
| gttaaaacta | ttacctatac | tgactcttcc | ggtgccgcca | gttctccaac | cgcggtcaaa | 1080 |
| ctgggcggag | atgatggcaa | aacagaagtg | gtcgatattg | atggtaaaac | atacgattct | 1140 |
| gccgatttaa | atggcggtaa | tctgcaaaca | ggtttgactg | ctggtggtga | ggctctgact | 1200 |
| gctgttgcaa | atggtaaaac | cacgatccg | ctgaaagcgc | tggacgatgc | tatcgcatct | 1260 |
| gtagacaaat | tccgttcttc | cctcggtgcg | gtgcaaaacc | gtctggattc | cgcggttacc | 1320 |
| aacctgaaca | cacccactac | caacctgtct | gaagcgcagt | cccgtattca | ggacgccgac | 1380 |
| tatgcgaccg | aagtgtccaa | tatgtcgaaa | gcgcagatca | tccagcaggc | cggtaactcc | 1440 |
| gtgttggcaa | aagctaacca | ggtaccgcag | caggttctgt | ctctgctgca | gggtaagctt | 1500 |
| ggaaccaatg | ctgccaatca | agcagcctat | caaaaagccc | ttgctgctta | tcaggctgaa | 1560 |
| ctgaaacgtg | ttcaggaagc | taatgcagcc | gccaaagccg | cttatgatac | tgctgtagca | 1620 |

```
gcaaataatg ccaaaaatac agaaattgcc gctgccaatg aagaaattag aaaacgcaat    1680
gcaacggcca aagctgaata tgagactaag ttagctcaat atcaagctga actaaagcgt    1740
gttcaggaag ctaatgccgc aaacgaagca gactatcaag ctaaattgac cgcctatcaa    1800
acagagcttg ctcgtgttca aaaagccaat gcggatgcta agcgaccta tgaagcagct     1860 gtagcagcaa ataatgccaa aaatgcggca ctcacagctg aaaatactgc aattaagcaa    1920
cgcaatgaga atgctaaggc gactatgaa gctgcactca gcaatatga ggccgatttg      1980 gcagcggtga aaaagctaa tgccgcaaac gaagcagact atcaagctaa attgaccgcc    2040
tatcaaacag agctcgctcg cgttcaaaaa gccaatgcgg atgctaaagc ggcctatgaa    2100
gcagctgtag cagcaaataa tgccgcaaat gcagcgctca cagctgaaaa tactgcaatt    2160
aagaagcgca atgcggatgc taaagctgat tacgaagcaa aacttgctaa gtatcaagca    2220
gatcttgcca atatcaaaa agatttagca gactatccag ttaagttaaa ggcatacgaa     2280
gatgaacaaa cttctattaa agctgcactg gcagaacttg aaaaacataa aaatgaagac    2340
ggaaacttaa cagaaccatc tgctcaaaat ttggtctatg atcttgagcc aaatgcgaac    2400
ttatctttga caacagatgg gaagttcctt aaggcttctg ctgtggatga tgcttttagc    2460
aaaagcactt caaaagcaaa atatgaccaa aaaattcttc aattagatga tctagatatc    2520
actaacttag aacaatctaa tgatgttgct tcttctatgg agcttatgg gaattttggt     2580 gataaagctg gctggtcaac gacagtaagc aataactcac aggttaaatg gggatcggta    2640
cttttagagc gcggtcaaag cgcaacagct acatacacta acctgcagaa ttcttattac    2700
aatggtaaaa agatttctaa aattgtctac aagtatacag tggaccctaa gtccaagttt    2760
caaggtcaaa aggtttggtt aggtattttt accgatccaa ctttaggtgt ttttgcttct    2820
gcttatacag gtcaagttga aaaaacact tctatttta ttaaaaatga attcactttc       2880
tatgacgaag atggaaaacc aattaatttt gataatgccc ttctctcagt agcttctctt    2940
aaccgtgaac ataactctat tgagatggct aaagattata gtggtaaatt tgtcaaaatc    3000
tctggttcat ctattggtga aaagaatggc atgatttatg ctacagatac tcttaacttt    3060
aaacagggtg aaggtggctc tcgctggact atgtataaaa atagtcaagc tggttcagga    3120
tgggatagtt cagatgcgcc gaattcttgg tatggagcag gggctattaa atgtctggt     3180 ccgaataacc atgttactgt aggagcaact tctgcaacaa atgtaatgcc agtttctgac    3240
atgcctgttg ttcctggtaa ggacaatact gatggcaaaa aaccaaatat ttggtattct    3300
ttaaatggta aaatccgtgc ggttaatgtt cctaaagtta ctaaggaaaa acccacacct    3360
ccggttaaac caacagctcc aactaaacca acttatgaaa cagaaaagcc attaaaaccg    3420
gcaccagtag ctccaaatta tgaaaaggag ccaacaccgc cgacaaggac accggatcaa    3480
gcagagccaa acaaacccac accgccgacc tatgaaacag aaaagccgtt ggagccagca    3540
cctgttgagc caacttatga gctcgagcac caccaccacc accac                    3585
```

<210> SEQ ID NO 6
<211> LENGTH: 1195
<212> TYPE: PRT
<213> ORGANISM: Artificial
<220> FEATURE:
<223> OTHER INFORMATION: KF-PAc fusion protein

<400> SEQUENCE: 6

Met Ala Gln Val Ile Asn Thr Asn Ser Leu Ser Leu Ile Thr Gln Asn
1               5                   10                  15

```
Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Leu Gln Arg Val Arg Glu Leu Thr
                85                  90                  95

Val Gln Ala Thr Thr Gly Thr Asn Ser Glu Ser Asp Leu Ser Ser Ile
                100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asn Gly Ser Met
    130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Gly Phe Ser Val Lys
                165                 170                 175

Asn Asn Asp Thr Val Thr Thr Ser Ala Pro Val Thr Ala Phe Gly Ala
            180                 185                 190

Thr Thr Thr Asn Asn Ile Lys Leu Thr Gly Ile Thr Leu Ser Thr Glu
    195                 200                 205

Ala Ala Thr Asp Thr Gly Gly Thr Asn Pro Ala Ser Ile Glu Gly Val
    210                 215                 220

Tyr Thr Asp Asn Gly Asn Asp Tyr Tyr Ala Lys Ile Thr Gly Gly Asp
225                 230                 235                 240

Asn Asp Gly Lys Tyr Tyr Ala Val Thr Val Ala Asn Asp Gly Thr Val
            245                 250                 255

Thr Met Ala Thr Gly Ala Thr Ala Asn Ala Thr Val Thr Asp Ala Asn
            260                 265                 270

Thr Thr Lys Ala Thr Thr Ile Thr Ser Gly Gly Thr Pro Val Gln Ile
        275                 280                 285

Asp Asn Thr Ala Gly Ser Ala Thr Ala Asn Leu Gly Ala Val Ser Leu
    290                 295                 300

Val Lys Leu Gln Asp Ser Lys Gly Asn Asp Thr Asp Thr Tyr Ala Leu
305                 310                 315                 320

Lys Asp Thr Asn Gly Asn Leu Tyr Ala Ala Asp Val Asn Glu Thr Thr
            325                 330                 335

Gly Ala Val Ser Val Lys Thr Ile Thr Tyr Thr Asp Ser Ser Gly Ala
        340                 345                 350

Ala Ser Ser Pro Thr Ala Val Lys Leu Gly Gly Asp Gly Lys Thr
        355                 360                 365

Glu Val Val Asp Ile Asp Gly Lys Thr Tyr Asp Ser Ala Asp Leu Asn
        370                 375                 380

Gly Gly Asn Leu Gln Thr Gly Leu Thr Ala Gly Glu Ala Leu Thr
385                 390                 395                 400

Ala Val Ala Asn Gly Lys Thr Thr Asp Pro Leu Lys Ala Leu Asp Asp
                405                 410                 415

Ala Ile Ala Ser Val Asp Lys Phe Arg Ser Ser Leu Gly Ala Val Gln
            420                 425                 430
```

```
Asn Arg Leu Asp Ser Ala Val Thr Asn Leu Asn Asn Thr Thr Asn
        435                 440                 445

Leu Ser Glu Ala Gln Ser Arg Ile Gln Asp Ala Asp Tyr Ala Thr Glu
450                 455                 460

Val Ser Asn Met Ser Lys Ala Gln Ile Ile Gln Gln Ala Gly Asn Ser
465                 470                 475                 480

Val Leu Ala Lys Ala Asn Gln Val Pro Gln Gln Val Leu Ser Leu Leu
                485                 490                 495

Gln Gly Lys Leu Gly Thr Asn Ala Ala Asn Gln Ala Ala Tyr Gln Lys
            500                 505                 510

Ala Leu Ala Ala Tyr Gln Ala Glu Leu Lys Arg Val Gln Glu Ala Asn
            515                 520                 525

Ala Ala Ala Lys Ala Ala Tyr Asp Thr Ala Val Ala Ala Asn Asn Ala
        530                 535                 540

Lys Asn Thr Glu Ile Ala Ala Ala Asn Glu Glu Ile Arg Lys Arg Asn
545                 550                 555                 560

Ala Thr Ala Lys Ala Glu Tyr Glu Thr Lys Leu Ala Gln Tyr Gln Ala
                565                 570                 575

Glu Leu Lys Arg Val Gln Glu Ala Asn Ala Ala Asn Glu Ala Asp Tyr
            580                 585                 590

Gln Ala Lys Leu Thr Ala Tyr Gln Thr Glu Leu Ala Arg Val Gln Lys
            595                 600                 605

Ala Asn Ala Asp Ala Lys Ala Thr Tyr Glu Ala Ala Val Ala Ala Asn
        610                 615                 620

Asn Ala Lys Asn Ala Ala Leu Thr Ala Glu Asn Thr Ala Ile Lys Gln
625                 630                 635                 640

Arg Asn Glu Asn Ala Lys Ala Thr Tyr Glu Ala Ala Leu Lys Gln Tyr
                645                 650                 655

Glu Ala Asp Leu Ala Ala Val Lys Lys Ala Asn Ala Ala Asn Glu Ala
            660                 665                 670

Asp Tyr Gln Ala Lys Leu Thr Ala Tyr Gln Thr Glu Leu Ala Arg Val
            675                 680                 685

Gln Lys Ala Asn Ala Asp Ala Lys Ala Ala Tyr Glu Ala Ala Val Ala
        690                 695                 700

Ala Asn Asn Ala Ala Asn Ala Ala Leu Thr Ala Glu Asn Thr Ala Ile
705                 710                 715                 720

Lys Lys Arg Asn Ala Asp Ala Lys Ala Asp Tyr Glu Ala Lys Leu Ala
                725                 730                 735

Lys Tyr Gln Ala Asp Leu Ala Lys Tyr Gln Lys Asp Leu Ala Asp Tyr
            740                 745                 750

Pro Val Lys Leu Lys Ala Tyr Glu Asp Glu Gln Thr Ser Ile Lys Ala
            755                 760                 765

Ala Leu Ala Glu Leu Glu Lys His Lys Asn Glu Asp Gly Asn Leu Thr
        770                 775                 780

Glu Pro Ser Ala Gln Asn Leu Val Tyr Asp Leu Glu Pro Asn Ala Asn
785                 790                 795                 800

Leu Ser Leu Thr Thr Asp Gly Lys Phe Leu Lys Ala Ser Ala Val Asp
                805                 810                 815

Asp Ala Phe Ser Lys Ser Thr Ser Lys Ala Lys Tyr Asp Gln Lys Ile
            820                 825                 830

Leu Gln Leu Asp Asp Leu Asp Ile Thr Asn Leu Glu Gln Ser Asn Asp
            835                 840                 845

Val Ala Ser Ser Met Glu Leu Tyr Gly Asn Phe Gly Asp Lys Ala Gly
```

```
                    850                 855                 860
Trp Ser Thr Thr Val Ser Asn Asn Ser Gln Val Lys Trp Gly Ser Val
865                 870                 875                 880

Leu Leu Glu Arg Gly Gln Ser Ala Thr Ala Thr Tyr Thr Asn Leu Gln
                    885                 890                 895

Asn Ser Tyr Tyr Asn Gly Lys Lys Ile Ser Lys Ile Val Tyr Lys Tyr
                    900                 905                 910

Thr Val Asp Pro Lys Ser Lys Phe Gln Gly Gln Lys Val Trp Leu Gly
                    915                 920                 925

Ile Phe Thr Asp Pro Thr Leu Gly Val Phe Ala Ser Ala Tyr Thr Gly
                    930                 935                 940

Gln Val Glu Lys Asn Thr Ser Ile Phe Ile Lys Asn Glu Phe Thr Phe
945                 950                 955                 960

Tyr Asp Glu Asp Gly Lys Pro Ile Asn Phe Asn Ala Leu Leu Ser
                    965                 970                 975

Val Ala Ser Leu Asn Arg Glu His Asn Ser Ile Glu Met Ala Lys Asp
                    980                 985                 990

Tyr Ser Gly Lys Phe Val Lys Ile Ser Gly Ser Ser Ile Gly Glu Lys
                    995                 1000                1005

Asn Gly Met Ile Tyr Ala Thr Asp Thr Leu Asn Phe Lys Gln Gly
    1010                1015                1020

Glu Gly Gly Ser Arg Trp Thr Met Tyr Lys Asn Ser Gln Ala Gly
    1025                1030                1035

Ser Gly Trp Asp Ser Ser Asp Ala Pro Asn Ser Trp Tyr Gly Ala
    1040                1045                1050

Gly Ala Ile Lys Met Ser Gly Pro Asn Asn His Val Thr Val Gly
    1055                1060                1065

Ala Thr Ser Ala Thr Asn Val Met Pro Val Ser Asp Met Pro Val
    1070                1075                1080

Val Pro Gly Lys Asp Asn Thr Asp Gly Lys Lys Pro Asn Ile Trp
    1085                1090                1095

Tyr Ser Leu Asn Gly Lys Ile Arg Ala Val Asn Val Pro Lys Val
    1100                1105                1110

Thr Lys Glu Lys Pro Thr Pro Pro Val Lys Pro Thr Ala Pro Thr
    1115                1120                1125

Lys Pro Thr Tyr Glu Thr Glu Lys Pro Leu Lys Pro Ala Pro Val
    1130                1135                1140

Ala Pro Asn Tyr Glu Lys Glu Pro Thr Pro Thr Arg Thr Pro
    1145                1150                1155

Asp Gln Ala Glu Pro Asn Lys Pro Thr Pro Thr Tyr Glu Thr
    1160                1165                1170

Glu Lys Pro Leu Glu Pro Ala Pro Val Glu Pro Thr Tyr Glu Leu
    1175                1180                1185

Glu His His His His His
    1190                1195

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7
gcgccatggc acaagtcatt aatacc                                          26
```

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
aacaagctta ccctgcagca gagacagaac 30

<210> SEQ ID NO 9
<211> LENGTH: 28
<212> TYPE: DNA
<213> ORGANISM: Artificial
<220> FEATURE:
<223> OTHER INFORMATION: Primer

<400> SEQUENCE: 9
tcaaagcttg gaaccaatgc tgccaatc 28

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
acgtctcgag ctcataagtt ggctcaacag 30

<210> SEQ ID NO 11
<211> LENGTH: 2880
<212> TYPE: DNA
<213> ORGANISM: Artificial
<220> FEATURE:
<223> OTHER INFORMATION: KFD2-PAc fusion protein encoding sequence

<400> SEQUENCE: 11
atggcacaag tcattaatac caacagcctc tcgctgatca ctcaaaataa tatcaacaag 60
aaccagtctg cgctgtcgag ttctatcgag cgtctgtctt ctggcttgcg tattaacagc 120
gcgaaggatg acgcagcggg tcaggcgatt gctaaccgtt tcacctctaa cattaaaggc 180
ctgactcagg cggcccgtaa cgccaacgac ggtatctccg ttgcgcagac caccgaaggc 240
gcgctgtccg aaatcaacaa caacttacag cgtgtgcgtg aactgacggt acaggccact 300
accggtacta actctgagtc tgatctgtct tctatccagg acgaaattaa atcccgtctg 360
gatgaaattg accgcgtatc tggtcagacc cagttcaacg gcgtgaacgt gctggcaaaa 420
aatggctcca tgaaaatcca ggttggcgca aatgataacc agactatcac tatcgatctg 480
aagcagattg atgctaaaac tcttggcctt gatgctagcg gaaccaatgc tgccaatcaa 540
gcagcctatc aaaaagccct tgctgcttat caggctgaac tgaaacgtgt tcaggaagct 600
aatgcagccg ccaaagccgc ttatgatact gctgtagcag caaataatgc caaaaataca 660
gaaattgccg ctgccaatga agaaattaga aaacgcaatg caacggccaa agctgaatat 720
gagactaagt tagctcaata tcaagctgaa ctaaagcgtg ttcaggaagc taatgccgca 780
aacgaagcag actatcaagc taaattgacc gcctatcaaa cagagcttgc tcgtgttcaa 840
aaagccaatg cggatgctaa agcgacctat gaagcagctg tagcagcaaa taatgccaaa 900
aatgcggcac tcacagctga aaatactgca attaagcaac gcaatgagaa tgctaaggcg 960

```
acttatgaag ctgcactcaa gcaatatgag gccgatttgg cagcggtgaa aaaagctaat    1020
gccgcaaacg aagcagacta tcaagctaaa ttgaccgcct atcaaacaga gctcgctcgc    1080
gttcaaaaag ccaatgcgga tgctaaagcg gcctatgaag cagctgtagc agcaaataat    1140
gccgcaaatg cagcgctcac agctgaaaat actgcaatta agaagcgcaa tgcggatgct    1200
aaagctgatt acgaagcaaa acttgctaag tatcaagcag atcttgccaa atatcaaaaa    1260
gatttagcag actatccagt taagttaaag gcatacgaag atgaacaaac ttctattaaa    1320
gctgcactgg cagaacttga aaaacataaa aatgaagacg aaacttaac agaaccatct    1380 gctcaaaatt tggtctatga tcttgagcca atgcgaact tatctttgac aacagatggg    1440
aagttcctta aggcttctgc tgtggatgat gcttttagca aaagcacttc aaaagcaaaa    1500
tatgaccaaa aaattcttca attagatgat ctagatatca ctaacttaga acaatctaat    1560
gatgttgctt cttctatgga gctttatggg aattttggtg ataaagctgg ctggtcaacg    1620
acagtaagca ataactcaca ggttaaatgg ggatcggtac ttttagagcg cggtcaaagc    1680
gcaacagcta catacactaa cctgcagaat tcttattaca atggtaaaaa gatttctaaa    1740
attgtctaca gtatacagt ggaccctaag tccaagtttc aaggtcaaaa ggtttggtta    1800 ggtatttta ccgatccaac tttaggtgtt tttgcttctg cttatacagg tcaagttgaa    1860 aaaacactt ctatttttat taaaaatgaa ttcactttct atgacgaaga tggaaaacca    1920
attaattttg ataatgccct tctctcagta gcttctctta accgtgaaca taactctatt    1980
gagatggcta agattatag tggtaaattt gtcaaaatct ctggttcatc tattggtgaa    2040
aagaatggca tgatttatgc tacagatact cttaacttta aacagggtga aggtggctct    2100
cgctggacta tgtataaaaa tagtcaagct ggttcaggat gggatagttc agatgcgccg    2160
aattcttggt atggagcagg ggctattaaa atgtctggtc gaataacca tgttactgta    2220 ggagcaactt ctgcaacaaa tgtaatgcca gtttctgaca tgcctgttgt tcctggtaag    2280
gacaatactg atggcaaaaa accaaatatt tggtattctt taaatggtaa aatccgtgcg    2340
gttaatgttc ctaaagttac taaggaaaaa cccacacctc cggttaaacc aacagctcca    2400
actaaaccaa cttatgaaac agaaaagcca ttaaaaccgg caccagtagc tccaaaattat    2460 gaaaaggagc caacaccgcc gacaaggaca ccggatcaag cagagccaaa caaacccaca    2520
ccgccgacct atgaaacaga aaagccgttg gagccagcac ctgttgagcc aacttatgag    2580
acgacggatc cgctgaaagc gctggacgat gctatcgcat ctgtagacaa attccgttct    2640
tccctcggtg cggtgcaaaa ccgtctggat tccgcggtta ccaacctgaa caacaccact    2700
accaacctgt ctgaagcgca gtcccgtatt caggacgccg actatgcgac cgaagtgtcc    2760
aatatgtcga aagcgcagat catccagcag gccgtaact ccgtgttggc aaaagctaac    2820
caggtaccgc agcaggttct gtctctgctg cagggtctcg agcaccacca ccaccaccac    2880
```

<210> SEQ ID NO 12
<211> LENGTH: 960
<212> TYPE: PRT
<213> ORGANISM: Artificial
<220> FEATURE:
<223> OTHER INFORMATION: KFD2-PAc fusion protein

<400> SEQUENCE: 12

```
Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30
```

```
Ser Ser Gly Leu Arg Ile Asn Ser Ala Lys Asp Asp Ala Gly Gln
        35                  40                  45

Ala Ile Ala Asn Arg Phe Thr Ser Asn Ile Lys Gly Leu Thr Gln Ala
 50                  55                  60

Ala Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Val Arg Glu Leu Thr
                 85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asn Gly Ser Met
        130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Ala Ser Gly Thr Asn
                165                 170                 175

Ala Ala Asn Gln Ala Ala Tyr Gln Lys Ala Leu Ala Ala Tyr Gln Ala
            180                 185                 190

Glu Leu Lys Arg Val Gln Glu Ala Asn Ala Ala Lys Ala Ala Tyr
            195                 200                 205

Asp Thr Ala Val Ala Ala Asn Asn Ala Lys Asn Thr Glu Ile Ala Ala
            210                 215                 220

Ala Asn Glu Glu Ile Arg Lys Arg Asn Ala Thr Ala Lys Ala Glu Tyr
225                 230                 235                 240

Glu Thr Lys Leu Ala Gln Tyr Gln Ala Glu Leu Lys Arg Val Gln Glu
                245                 250                 255

Ala Asn Ala Ala Asn Glu Ala Asp Tyr Gln Ala Lys Leu Thr Ala Tyr
            260                 265                 270

Gln Thr Glu Leu Ala Arg Val Gln Lys Ala Asn Ala Asp Ala Lys Ala
            275                 280                 285

Thr Tyr Glu Ala Ala Val Ala Ala Asn Asn Ala Lys Asn Ala Ala Leu
        290                 295                 300

Thr Ala Glu Asn Thr Ala Ile Lys Gln Arg Asn Glu Asn Ala Lys Ala
305                 310                 315                 320

Thr Tyr Glu Ala Ala Leu Lys Gln Tyr Glu Ala Asp Leu Ala Ala Val
                325                 330                 335

Lys Lys Ala Asn Ala Ala Asn Glu Ala Asp Tyr Gln Ala Lys Leu Thr
            340                 345                 350

Ala Tyr Gln Thr Glu Leu Ala Arg Val Gln Lys Ala Asn Ala Asp Ala
        355                 360                 365

Lys Ala Ala Tyr Glu Ala Val Ala Ala Asn Asn Ala Ala Asn Ala
370                 375                 380

Ala Leu Thr Ala Glu Asn Thr Ala Ile Lys Lys Arg Asn Ala Asp Ala
385                 390                 395                 400

Lys Ala Asp Tyr Glu Ala Lys Leu Ala Lys Tyr Gln Ala Asp Leu Ala
                405                 410                 415

Lys Tyr Gln Lys Asp Leu Ala Asp Tyr Pro Val Lys Leu Lys Ala Tyr
            420                 425                 430

Glu Asp Glu Gln Thr Ser Ile Lys Ala Ala Leu Ala Glu Leu Glu Lys
            435                 440                 445
```

```
His Lys Asn Glu Asp Gly Asn Leu Thr Glu Pro Ser Ala Gln Asn Leu
    450                 455                 460
Val Tyr Asp Leu Glu Pro Asn Ala Asn Leu Ser Leu Thr Thr Asp Gly
465                 470                 475                 480
Lys Phe Leu Lys Ala Ser Ala Val Asp Ala Phe Ser Lys Ser Thr
                485                 490                 495
Ser Lys Ala Lys Tyr Asp Gln Lys Ile Leu Gln Leu Asp Asp Leu Asp
                500                 505                 510
Ile Thr Asn Leu Glu Gln Ser Asn Asp Val Ala Ser Ser Met Glu Leu
        515                 520                 525
Tyr Gly Asn Phe Gly Asp Lys Ala Gly Trp Ser Thr Thr Val Ser Asn
530                 535                 540
Asn Ser Gln Val Lys Trp Gly Ser Val Leu Leu Glu Arg Gly Gln Ser
545                 550                 555                 560
Ala Thr Ala Thr Tyr Thr Asn Leu Gln Asn Ser Tyr Tyr Asn Gly Lys
                565                 570                 575
Lys Ile Ser Lys Ile Val Tyr Lys Tyr Thr Val Asp Pro Lys Ser Lys
                580                 585                 590
Phe Gln Gly Gln Lys Val Trp Leu Gly Ile Phe Thr Asp Pro Thr Leu
                595                 600                 605
Gly Val Phe Ala Ser Ala Tyr Thr Gly Gln Val Glu Lys Asn Thr Ser
        610                 615                 620
Ile Phe Ile Lys Asn Glu Phe Thr Phe Tyr Asp Glu Asp Gly Lys Pro
625                 630                 635                 640
Ile Asn Phe Asp Asn Ala Leu Leu Ser Val Ala Ser Leu Asn Arg Glu
                645                 650                 655
His Asn Ser Ile Glu Met Ala Lys Asp Tyr Ser Gly Lys Phe Val Lys
                660                 665                 670
Ile Ser Gly Ser Ser Ile Gly Glu Lys Asn Gly Met Ile Tyr Ala Thr
                675                 680                 685
Asp Thr Leu Asn Phe Lys Gln Gly Glu Gly Gly Ser Arg Trp Thr Met
        690                 695                 700
Tyr Lys Asn Ser Gln Ala Gly Ser Gly Trp Asp Ser Ser Asp Ala Pro
705                 710                 715                 720
Asn Ser Trp Tyr Gly Ala Gly Ala Ile Lys Met Ser Gly Pro Asn Asn
                725                 730                 735
His Val Thr Val Gly Ala Thr Ser Ala Thr Asn Val Met Pro Val Ser
                740                 745                 750
Asp Met Pro Val Val Pro Gly Lys Asp Asn Thr Asp Gly Lys Lys Pro
                755                 760                 765
Asn Ile Trp Tyr Ser Leu Asn Gly Lys Ile Arg Ala Val Asn Val Pro
        770                 775                 780
Lys Val Thr Lys Glu Lys Pro Thr Pro Pro Val Lys Pro Thr Ala Pro
785                 790                 795                 800
Thr Lys Pro Thr Tyr Glu Thr Glu Lys Pro Leu Lys Pro Ala Pro Val
                805                 810                 815
Ala Pro Asn Tyr Glu Lys Glu Pro Thr Pro Thr Arg Thr Pro Asp
                820                 825                 830
Gln Ala Glu Pro Asn Lys Pro Thr Pro Pro Tyr Glu Thr Glu Lys
        835                 840                 845
Pro Leu Glu Pro Ala Pro Val Glu Pro Thr Tyr Glu Thr Thr Asp Pro
850                 855                 860
Leu Lys Ala Leu Asp Asp Ala Ile Ala Ser Val Asp Lys Phe Arg Ser
```

```
                865                 870                 875                 880
Ser Leu Gly Ala Val Gln Asn Arg Leu Asp Ser Ala Val Thr Asn Leu
                    885                 890                 895

Asn Asn Thr Thr Thr Asn Leu Ser Glu Ala Gln Ser Arg Ile Gln Asp
                    900                 905                 910

Ala Asp Tyr Ala Thr Glu Val Ser Asn Met Ser Lys Ala Gln Ile Ile
            915                 920                 925

Gln Gln Ala Gly Asn Ser Val Leu Ala Lys Ala Asn Gln Val Pro Gln
    930                 935                 940

Gln Val Leu Ser Leu Leu Gln Gly Leu Glu His His His His His His
945                 950                 955                 960

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13
tatagctagc ggaaccaatg ctgccaatc                                          29

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
attaggatcc gtcgtctcat aagttggctc                                         30

<210> SEQ ID NO 15
<211> LENGTH: 1497
<212> TYPE: DNA
<213> ORGANISM: Escherichia coli

<400> SEQUENCE: 15
atggcacaag tcattaatac aacagcctc tcgctgatca ctcaaaataa tatcaacaag         60
aaccagtctg cgctgtcgag ttctatcgag cgtctgtctt ctggcttgcg tattaacagc      120
gcgaaggatg acgcagcggg tcaggcgatt gctaaccgtt tcacctctaa cattaaaggc      180
ctgactcagg cggcccgtaa cgccaacgac ggtatctccg ttgcgcagac caccgaaggc      240
gcgctgtccg aaatcaacaa caacttacag cgtgtgcgtg aactgacggt acaggccact      300
accggtacta actctgagtc tgatctgtct tctatccagg acgaaattaa atcccgtctg      360
gatgaaattg accgcgtatc tggtcagacc cagttcaacg gcgtgaacgt gctggcaaaa      420
aatggctcca tgaaaatcca ggttggcgca atgataacc agactatcac tatcgatctg      480 aagcagatt atgctaaaac tcttggcctt gatggtttta cgttaaaaa taacgataca      540 gttaccacta gtgctccagt aactgctttt ggtgctacca ccacaaacaa tattaaactt      600
actggaatta ccctttctac ggaagcagcc actgatactg gcggaactaa cccagcttca      660
attgagggtg tttatactga taatggtaat gattactatg cgaaaatcac cggtggtgat      720
aacgatggga gtattacgc agtaacagtt gctaatgatg gtacagtgac aatggcgact      780
ggagcaacgg caaatgcaac tgtaactgat gcaaatacta ctaaagctac aactatcact      840
tcaggcggta cacctgttca gattgataat actgcaggtt ccgcaactgc caaccttggt      900
```

```
gctgttagct tagtaaaact gcaggattcc aagggtaatg ataccgatac atatgcgctt   960
aaagatacaa atggcaatct ttacgctgcg gatgtgaatg aaactactgg tgctgtttct  1020
gttaaaacta ttacctatac tgactcttcc ggtgccgcca gttctccaac cgcggtcaaa  1080
ctgggcggag atgatggcaa aacagaagtg gtcgatattg atggtaaaac atacgattct  1140
gccgatttaa atggcggtaa tctgcaaaca ggtttgactg ctggtggtga ggctctgact  1200
gctgttgcaa atggtaaaac cacggatccg ctgaaagcgc tggacgatgc tatcgcatct  1260
gtagacaaat ccgttcttc cctcggtgcg gtgcaaaacc gtctggattc cgcggttacc  1320
aacctgaaca acaccactac caacctgtct gaagcgcagt cccgtattca ggacgccgac  1380
tatgcgaccg aagtgtccaa tatgtcgaaa gcgcagatca tccagcaggc cggtaactcc  1440
gtgttggcaa aagctaacca ggtaccgcag caggttctgt ctctgctgca gggttaa    1497
```

<210> SEQ ID NO 16
<211> LENGTH: 498
<212> TYPE: PRT
<213> ORGANISM: Escherichia coli

<400> SEQUENCE: 16

```
Met Ala Gln Val Ile Asn Thr Asn Ser Leu Ser Leu Ile Thr Gln Asn
  1               5                  10                  15

Asn Ile Asn Lys Asn Gln Ser Ala Leu Ser Ser Ser Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ser Asn Ile Lys Gly Leu Thr Gln Ala
     50                  55                  60

Ala Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Val Arg Glu Leu Thr
                 85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asn Gly Ser Met
    130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Gly Phe Ser Val Lys
                165                 170                 175

Asn Asn Asp Thr Val Thr Thr Ser Ala Pro Val Thr Ala Phe Gly Ala
            180                 185                 190

Thr Thr Thr Asn Asn Ile Lys Leu Thr Gly Ile Thr Leu Ser Thr Glu
        195                 200                 205

Ala Ala Thr Asp Thr Gly Gly Thr Asn Pro Ala Ser Ile Glu Gly Val
    210                 215                 220

Tyr Thr Asp Asn Gly Asn Asp Tyr Tyr Ala Lys Ile Thr Gly Gly Asp
225                 230                 235                 240

Asn Asp Gly Lys Tyr Tyr Ala Val Thr Val Ala Asn Asp Gly Thr Val
                245                 250                 255

Thr Met Ala Thr Gly Ala Thr Ala Asn Ala Thr Val Thr Asp Ala Asn
            260                 265                 270
```

-continued

```
Thr Thr Lys Ala Thr Thr Ile Thr Ser Gly Gly Thr Pro Val Gln Ile
        275                 280                 285

Asp Asn Thr Ala Gly Ser Ala Thr Ala Asn Leu Gly Ala Val Ser Leu
        290                 295                 300

Val Lys Leu Gln Asp Ser Lys Gly Asn Asp Thr Asp Thr Tyr Ala Leu
305                 310                 315                 320

Lys Asp Thr Asn Gly Asn Leu Tyr Ala Ala Asp Val Asn Glu Thr Thr
                325                 330                 335

Gly Ala Val Ser Val Lys Thr Ile Thr Tyr Thr Asp Ser Ser Gly Ala
            340                 345                 350

Ala Ser Ser Pro Thr Ala Val Lys Leu Gly Gly Asp Asp Gly Lys Thr
        355                 360                 365

Glu Val Val Asp Ile Asp Gly Lys Thr Tyr Asp Ser Ala Asp Leu Asn
        370                 375                 380

Gly Gly Asn Leu Gln Thr Gly Leu Thr Ala Gly Gly Glu Ala Leu Thr
385                 390                 395                 400

Ala Val Ala Asn Gly Lys Thr Thr Asp Pro Leu Lys Ala Leu Asp Asp
                405                 410                 415

Ala Ile Ala Ser Val Asp Lys Phe Arg Ser Ser Leu Gly Ala Val Gln
            420                 425                 430

Asn Arg Leu Asp Ser Ala Val Thr Asn Leu Asn Asn Thr Thr Thr Asn
        435                 440                 445

Leu Ser Glu Ala Gln Ser Arg Ile Gln Asp Ala Asp Tyr Ala Thr Glu
    450                 455                 460

Val Ser Asn Met Ser Lys Ala Gln Ile Ile Gln Gln Ala Gly Asn Ser
465                 470                 475                 480

Val Leu Ala Lys Ala Asn Gln Val Pro Gln Gln Val Leu Ser Leu Leu
                485                 490                 495

Gln Gly
```